(12) United States Patent
Unis et al.

(10) Patent No.: US 11,839,548 B2
(45) Date of Patent: *Dec. 12, 2023

(54) APPARATUS, METHOD AND SYSTEM FOR PROVIDING CUSTOMIZABLE BONE IMPLANTS

(71) Applicant: ICAHN SCHOOL OF MEDICINE AT MOUNT SINAI, New York, NY (US)

(72) Inventors: Douglas B. Unis, Brooklyn, NY (US); Sulaiman Somani, New York, NY (US); Anthony B. Costa, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/061,814

(22) Filed: Dec. 5, 2022

(65) Prior Publication Data

US 2023/0103348 A1 Apr. 6, 2023

Related U.S. Application Data

(63) Continuation of application No. 17/176,653, filed on Feb. 16, 2021, now Pat. No. 11,517,440, which is a
(Continued)

(51) Int. Cl.
*A61F 2/30* (2006.01)
*B22F 10/80* (2021.01)
(Continued)

(52) U.S. Cl.
CPC ............ *A61F 2/30942* (2013.01); *A61F 2/28* (2013.01); *A61F 2/30* (2013.01); *A61F 2/3601* (2013.01);
(Continued)

(58) Field of Classification Search
CPC .......... A61F 2/30942; A61F 2/28; A61F 2/30; A61F 2/3601; A61F 2002/3092;
(Continued)

(56) References Cited

U.S. PATENT DOCUMENTS 7,517,365 B2    4/2009   Carignan et al.
10,945,848 B2   3/2021   Unis et al.
(Continued)

FOREIGN PATENT DOCUMENTS

EP    1862151       12/2007
WO    2017177182 A1  10/2017
WO    2020214804 A1  10/2020

OTHER PUBLICATIONS

IP Australia, Examination Report No. 1 dated Jun. 21, 2021, 3 pages, Australia.
(Continued)

*Primary Examiner* — Michael J Brown
(74) *Attorney, Agent, or Firm* — Heslin Rothenberg Farley & Mesiti PC

(57) ABSTRACT

The present invention includes a method for generating a three-dimensional model of a bone. The method may further include generating a cut plan for excavating a portion of the bone according to the cut plan to allow the insertion of a custom implant. In a particular arrangement, the method may includes excavating the bone with an autonomous extremity excavator utilizing the cut plan generated by a processor. In a further arrangement, the method may include generating a digital model of a custom implant and generating, using the digital model, a physical model sharing the same dimensions as the digital module using manufacturing device.

28 Claims, 17 Drawing Sheets

Related U.S. Application Data continuation of application No. 16/153,334, filed on Oct. 5, 2018, now Pat. No. 10,945,848, which is a continuation of application No. PCT/US2017/026681, filed on Apr. 7, 2017.

(60) Provisional application No. 62/319,710, filed on Apr. 7, 2016.

(51) Int. Cl.
| | |
|---|---|
| *A61F 2/36* | (2006.01) |
| *A61F 2/28* | (2006.01) |
| *G06F 30/20* | (2020.01) |
| *B33Y 30/00* | (2015.01) |
| *B33Y 50/00* | (2015.01) |
| *G05B 19/4099* | (2006.01) |
| *B22F 10/00* | (2021.01) |
| *G05B 19/40* | (2006.01) |
| *B22F 10/28* | (2021.01) |

(52) U.S. Cl.
CPC ............. *B22F 10/80* (2021.01); *B33Y 30/00* (2014.12); *B33Y 50/00* (2014.12); *G05B 19/4099* (2013.01); *G06F 30/20* (2020.01); *A61F 2002/3092* (2013.01); *A61F 2002/3096* (2013.01); *A61F 2002/3097* (2013.01); *A61F 2002/30943* (2013.01); *A61F 2002/30948* (2013.01); *A61F 2002/30952* (2013.01); *A61F 2002/30953* (2013.01); *A61F 2002/30957* (2013.01); *A61F 2002/30962* (2013.01); *A61F 2002/30968* (2013.01); *A61F 2002/30985* (2013.01); *B22F 10/00* (2021.01); *B22F 10/28* (2021.01); *G05B 2219/35134* (2013.01); *G05B 2219/49007* (2013.01)

(58) Field of Classification Search
CPC .. A61F 2002/30948; A61F 2002/30952; A61F 2002/30957; A61F 2002/3096; A61F 2002/30962; A61F 2002/3097; A61F 2002/30985; B22F 10/80; B33Y 30/00; B33Y 50/00; G05B 19/4099; G05B 2219/35134; G05B 2219/49007; G06F 30/20

USPC ........................................................ 700/98
See application file for complete search history.

(56) References Cited

U.S. PATENT DOCUMENTS

| | | | |
|---|---|---|---|
| 11,517,440 B2* | 12/2022 | Unis | .................. A61F 2/30942 |
| 2007/0118243 A1 | 5/2007 | Schroeder | |
| 2008/0009954 A1 | 1/2008 | Mueller et al. | |
| 2011/0282473 A1* | 11/2011 | Pavlovskaia | ........... A61B 6/032 |
| | | | 700/98 |
| 2013/0039592 A1 | 2/2013 | Lang et al. | |
| 2013/0197866 A1 | 8/2013 | Wuestemann et al. | |
| 2014/0136154 A1 | 5/2014 | Bojarski et al. | |
| 2014/0195030 A1* | 7/2014 | Farwell | .................. A61B 34/10 |
| | | | 700/98 |
| 2014/0263214 A1 | 9/2014 | Dahotre et al. | |
| 2015/0030224 A1 | 1/2015 | Mahfouz | |
| 2015/0080717 A1 | 3/2015 | Ferko | |
| 2015/0119987 A1 | 4/2015 | Davignon et al. | |
| 2015/0324114 A1 | 11/2015 | Hurley et al. | |
| 2015/0328004 A1* | 11/2015 | Mafhouz | ............... A61F 2/2875 |
| | | | 700/98 |
| 2018/0263782 A1 | 9/2018 | Lang et al. | |
| 2019/0060079 A1 | 2/2019 | Unis et al. | |

OTHER PUBLICATIONS

International Search Report and Written Opinion issued in PCT/US2017/026681, and published as WO 2017/177182, dated Sep. 5, 2017, 14 pages, Sep. 5, 2017.

Extended European Search Report for European Application No. 17779938.4 dated Nov. 19, 2019, 7 pages, Nov. 19, 2019.

International Search Report and Written Opinion, issued in PCT/US2020/028499 (published as WO 2022/214804), dated Jul. 15, 2020, 14 pages.

International Preliminary Report on Patentability for International Application No. PCT/US2020/028499, dated Sep. 28, 2021, 13 pages, International Bureau of WIPO.

Extended European Search Report, EP Application No. 20791627.1, 7 pages, dated Nov. 28, 2022.

* cited by examiner

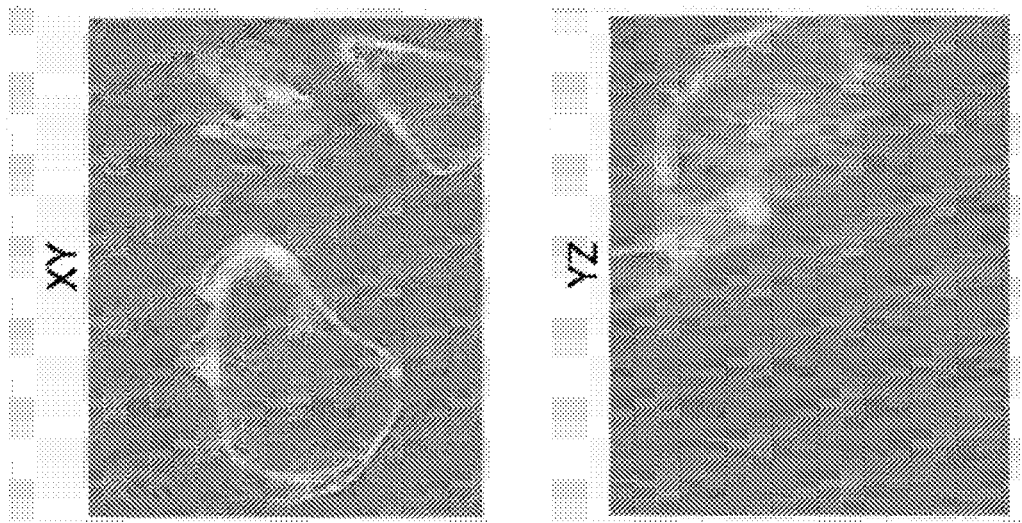
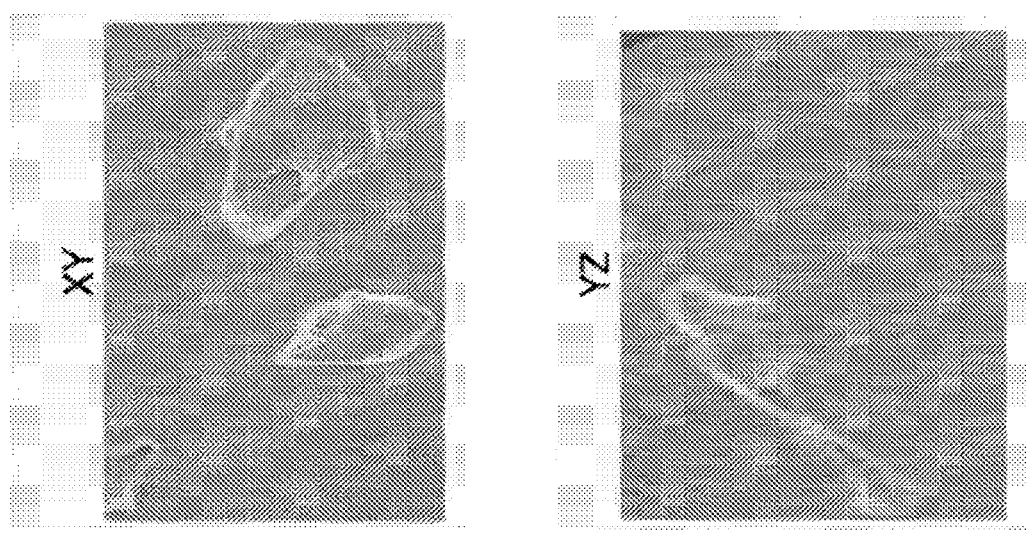
Fig. 4C

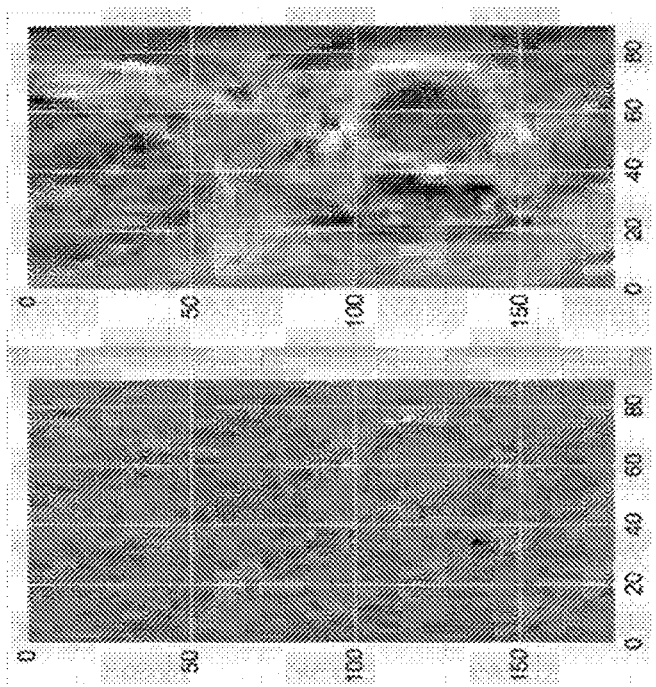
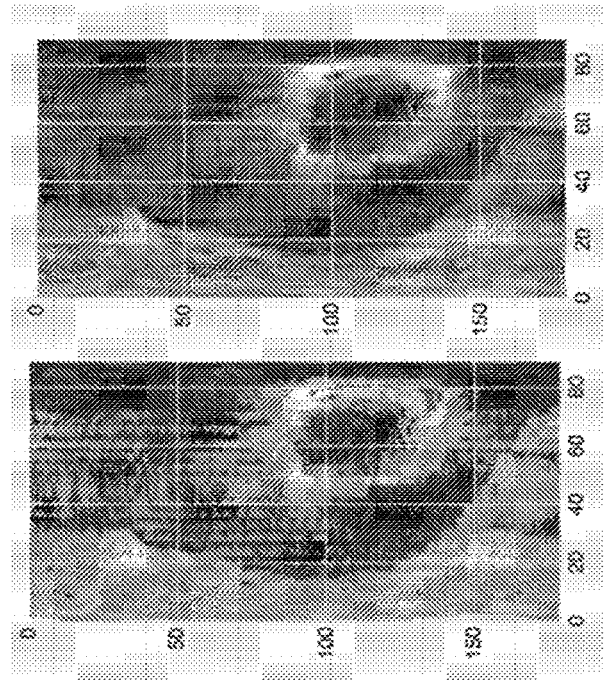
Fig. 6A

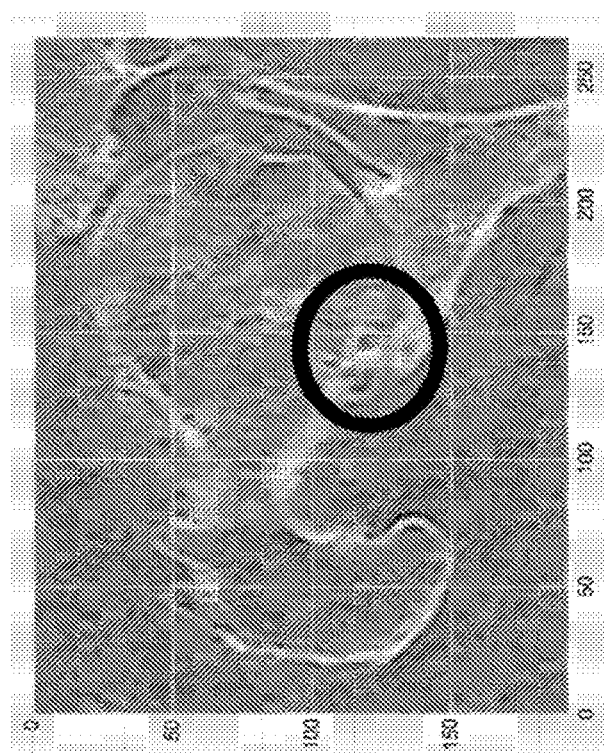
Fig. 6B

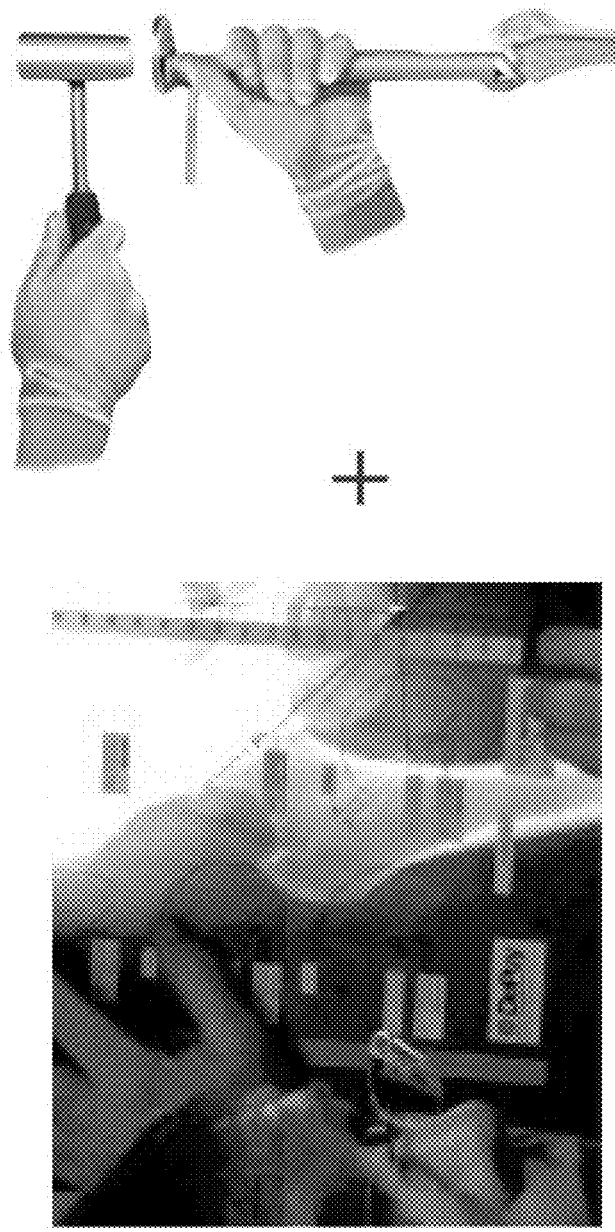
Fig. 12  Crude Planning and Execution (Prior Art)

APPARATUS, METHOD AND SYSTEM FOR PROVIDING CUSTOMIZABLE BONE IMPLANTS

CROSS REFERENCE TO RELATED APPLICATIONS

This application is a continuation of U.S. patent application Ser. No. 17/176,653, filed on Feb. 16, 2021, entitled "Apparatus, Method And System For Providing Customizable Bone Implants, which issued on Dec. 6, 2022, as U.S. Pat. No. 11,517,440, which application is a continuation of U.S. patent application Ser. No. 16/153,334, filed on Oct. 5, 2018, entitled "Apparatus, Method And System For Providing Customizable Bone Implants," which issued on Mar. 16, 2021, as U.S. Pat. No. 10,945,848, which application is a by-pass continuation of PCT Application No. PCT/US2017/026681 filed on Apr. 7, 2017, which PCT application claimed priority from U.S. Provisional Application 62/319,710 filed on Apr. 7, 2016, and which applications are incorporated herein by reference in their entireties.

TECHNICAL FIELD

The present invention describes systems and methods for generating a customizable bone implant and in particular, to generating short stem implants for use in hip arthroplasty in accordance with such systems and methods.

BACKGROUND

Hip arthroplasty, also known as hip replacement surgery, is a surgical procedure performed to alleviate hip pain due to chronic conditions such as arthritis. The surgical procedure entails replacing the hip joint with a prosthetic implant, typically called a femoral stem. Hip replacement is currently one of the most common types of orthopedic operation, although complications and device failure are common. During hip replacement, a surgeon removes the damaged sections of a patient's hip joint and replaces them with a prostatic implant usually constructed of metal and/or very hard plastic. This artificial joint (prosthesis) helps reduce pain and improve function. Most femoral stems are mass produced, non-custom implants that rely on manual bone preparation using broaches and/or reamers. In fact, techniques for preparing a femur to receive an implant have made little advancement over the decades. Surgical professionals are still required to manually file, usually with nothing more than a rasp, the bone of the femur in order to create a suitable receptacle for the implant within the bone.

Prosthetic implants used in hip replacement consist of three parts: the acetabular cup, the femoral stem component, and the articular interface. Some variation exists in the dimensions of the implant for different people and medical indications.

The femoral stem component is the component that fits in the femur (thigh bone). A portion of the bone is removed and a cavity is shaped to accept the femoral stem. The stem is then fixated to the bone to secure the implant. There are two types of fixation: cemented and uncemented. Cemented stems use acrylic bone cement to form a mantle between the stem and to the bone. Uncemented stems use friction, shape and surface coatings to stimulate bone to remodel and bond to the implant.

However, standard implants have poor cortical contact, i.e. the portion of the implant that is matched and in contact with bone. For standard implants the cortical contact values can be as low as 30-40% of surface area of the implant. Therefore, what are needed are systems and methods for producing custom stems that allow for improved fixation, performance and function. Current custom femoral stem designs are still produced at standard lengths and have poor cortical contact with the femur or other bone.

What is also needed in the art is the ability to automate bone mapping so that custom femoral stems can be generated from such automated models and maps.

There also exists a need for systems and methods that enable the automatic preparation of a femur for insertion of a custom designed implant. Such systems and methods can include generating or simulating three dimensional models of the implant insertion site, as well as a designed implant.

The current standard for creating high-fidelity, 3D patient-specific anatomical models from radiological scans (e.g., CT, MM, planar radiographs) involves the arduous process of fully-manual segmentation. This can take many hours depending on structure(s) of interest, the patient's clinical profile, acceptable tolerances, and the experience of the expert operator. To compound these issues, the most fundamental limitation of modern medical imaging science, resolution, places significant limitations on the quality of the output "ground truth" segmentation mask created for each case, while inter-rater variability is significant. Thus, perfect objectivity in segmentation, further blemished by parametric selections for image generation from the scanning process itself (for example, in CT scans, the choice of reconstruction kernel, current, and voltage choices can significantly affect the signal-to-noise ratio in the output scan) is difficult to achieve even within the bounds of the so-called gold standard. Given these limitations, the pursuit of relatively significantly faster and fully automated methods for segmentation are sought.

Thus, what is needed in the art is an improved method of obtaining high-fidelity anatomical models from radiological scans. The prior art teaches various techniques for segmenting CT scans such as Chu, Chengwen, Cheng Chen, Li Liu, and Guoyan Zheng. "FACTS: Fully Automatic CT Segmentation of a Hip Joint." Annals of Biomedical Engineering 43.5 (2014): 1247-259; Almeida, Diogo F., Rui B. Ruben, Joao Folgado, Paulo R. Fernandes, Emmanuel Audenaert, Benedict Verhegghe, and Matthieu De Beule. "Fully Automatic Segmentation of Femurs with Medullary Canal Definition in High and in Low Resolution CT Scans." Medical Engineering & Physics 38.12 (2016): 1474-480; and SOILLE, PIERRE. Morphological Image Analysis. N.p.: n.p., n.d. Springer-Verlag Berlin Heidelberg, all of which are herein incorporated by reference as if provided in their respective entireties. However, what is needed is a system and method that overcomes the limitations in the art and provides a system and method for obtaining fully autonomous and automatic outer cortical bone models from CT scan data.

It will be appreciated that the aforementioned discussion is one application of the present invention, namely, for generation of a femoral stem implant. However, the teachings described above can be used for other surgical sites and in particular, can be applied for other orthopedic implants, especially joint implants, such as for the shoulder, elbow, and knee.

SUMMARY

Provided herein is a method for use in digitally generating a custom implant, in which the method includes, for example, generating a three-dimensional digital model of the custom implant using at least data obtained from a three-dimensional digital representation of the patient's bone having at least data operably identifying cortical bone boundaries of the patient's bone. The method may further include generating the three-dimensional digital representation of the patient's bone, wherein the three-dimensional digital representation of the patient's bone comprises at least data operably identifying cortical bone boundaries of the patient's bone.

In one particular implementation, the present invention includes a system for generating a custom implant for a patient, in which the system includes, for example, a processor configured with code executing therein to transform digital bone data into a three-dimensional digital representation of the patient's bone, the processor further configured to generate, using an implant modeling application, a three-dimensional digital model of the custom implant for insertion into the bone, the three-dimensional digital representation of the bone including at least data operably identifying cortical bone boundaries of the patient's bone, the processor additionally configured to generate an excavation protocol for excavating bone from the selected bone such that a percent contact between an inner surface of a cortical bone region in the patient's bone and an outer surface of the custom implant is at least 30%, and a manufacturing device configured to generate the custom implant from the three-dimensional digital model of the custom implant.

In a further arrangement, the present invention includes a computer implemented method for generating a three-dimensional digital model of a custom implant, which includes, for example, generating, using code executing in a processor, a three-dimensional digital model of a patient's bone using at least information obtained from a three-dimensional scan having at least data operably identifying cortical bone boundaries of the scanned bone of the patient, where the three-dimensional digital model of the bone comprises an extraction portion and a remaining portion, the extraction portion corresponding to an anticipated removal of material from the bone, and building, using code executing in the processor, a three-dimensional digital model of the custom implant configured to replace the extraction portion in the three-dimensional digital model of the bone, wherein the three-dimensional digital model of the custom implant is configured to match the cortical bone boundaries features of the bone model using finite element analysis.

Provided herein is a system for generating a custom bone implant, the system in one potential arrangement, comprising a bone scanner configured to obtain bone scan data from a patient's bone, such as a femur; a processor configured with code executing therein to transform the bone data into a 3D model of the bone, the processor further configured to generate using a stem modeling application, a 3D digital model of a stem for insertion into the bone, the processor additionally configured to generate an excavation protocol for excavating bone from the femur such that the amount of bone contact between the bone and the implant is 50% or greater. The system also includes connections between the processor and an additive manufacturing device, the additive manufacturing device configured to receive data relating to the digital model of the implant and generate a 3D representation of the 3D model, including providing different areas of relative porosity and density. The invention further includes a processor controlled bone excavation device in communicative contact with the system described and configured to excavate bone from the patient femur according to the excavation protocol.

In one particular implementation, the present invention includes a method for generating a 3D model of a femur from scan data. The method including applying a threshold mask to the pixels representing the femur within the scan data, augmenting the threshold mask applied to pixels representing the femoral head using a shape modeling algorithm; identifying the pixels corresponding to the femoral neck using an intensity threshold, eroding the pixel intensity values for pixels not corresponding to the femoral head and neck and updating the pixels classified by the shape modeling algorithm, and outputting a 3D model of the femur.

In one particular implementation, the present invention includes a method for generating a 3D model of a femur from scan data and generating a cut plan for excavating a portion of the bone according to the cut plan to allow the insertion of a custom implant. In a particular arrangement, the method also includes excavating the bone with an autonomous extremity excavator utilizing the cut plan generated by a processor. In a further arrangement, the method includes generating a digital model of a custom implant and generating, using the digital model, a physical model sharing the same dimensions as the digital module using manufacturing device.

In a further arrangement, the present invention includes a method for generating a 3D model of a bone and generating a cut plan for excavating a portion of the bone according to the cut plan to allow the insertion of a custom implant. In a particular arrangement, the method also includes excavating the bone with an autonomous extremity excavator utilizing the cut plan generated by a processor. In a further arrangement, the method includes generating a digital model of a custom implant and generating, using the digital model, a physical model sharing the same dimensions as the digital module using manufacturing device.

The invention also includes a manufactured patient specific femoral stem wherein the length of the stem is not longer than 5 mm greater than the distance from the femur head to the base of the patient's lesser trochanter and is configured to achieve at least 60% available cortical bone contact.

These and other aspects, features and advantages of the present invention can be further appreciated from the following discussion of particular embodiments thereof.

BRIEF DESCRIPTION OF THE DRAWINGS

The foregoing and other features of the present invention will be more readily apparent from the following detailed description and drawings of one or more exemplary embodiments of the invention in which:

FIGS. 4A-C provide further details relating to the generation of a bone model in accordance with aspects described herein.

FIGS. 6A-C provide a chart detailing the effectiveness of the techniques described herein.

FIG. 12 provides an exemplary procedure found in the prior art.

DETAILED DESCRIPTION OF CERTAIN EMBODIMENTS

By way of overview and introduction, the systems, methods and apparatus described are directed to evaluating a patient's bone containing extremity for implantation within an implant. Commensurate with this evaluation, the systems and methods further include generating a computer model representative of the patient's bone (e.g. femur). Furthermore, the generated bone model identifies with sub-voxel (e.g. volumetric pixel data) accuracy, the location of "inner cortical bone" (i.e., the location of the inner surface of the cortical bone region) relative to "outer cortical bone" (i.e., the location of the outer surface of the cortical bone region). Using such a high fidelity bone model, a virtual representation of a proposed implant is generated that has a high degree of compatibility with the patient's bone.

The detailed system further enables modeling the interaction between the bone and implant in a computer simulation to optimize the conservation of bone and provide the highest level of cortical bone contact for the implant. Once the optimal design of an implant has been established, the implant is manufactured using an additive manufacturing device such as a 3-dimensional printer. The computer model is further used to simulate preparing the extremity for implantation of the implant. For example, the computer simulation enables the virtual evacuation of an extremity, such as a femur, in preparation for implantation of the implant. Once a suitable simulation of the excavation has been determined, an instruction set is generated for transmission to an extremity evacuation device, such as a computer controlled bone milling apparatus. Once the bone is excavated, the manufactured custom implant is installed by medical professionals.

For ease of description and figures, the following description references a femur and the implantation of a femoral stem implant. However, those possessing an ordinary level of requisite skill in the relevant art will appreciate that other extremities and implants are suitable for use with the foregoing systems, methods and apparatuses. Likewise, the various steps, procedures and work-flows are presented only as an example and in no way limit the systems, methods or apparatus described to performing their respective tasks or outcomes in different time-frames or orders. For example, the teachings of the present invention can be applied to any orthopedic implants, especially joints implants, such as the shoulder, elbow, and knee. Therefore, the systems and methods described herein can be implemented in other treatments sites that have similar anatomical considerations.

System Overview

Figure 1:
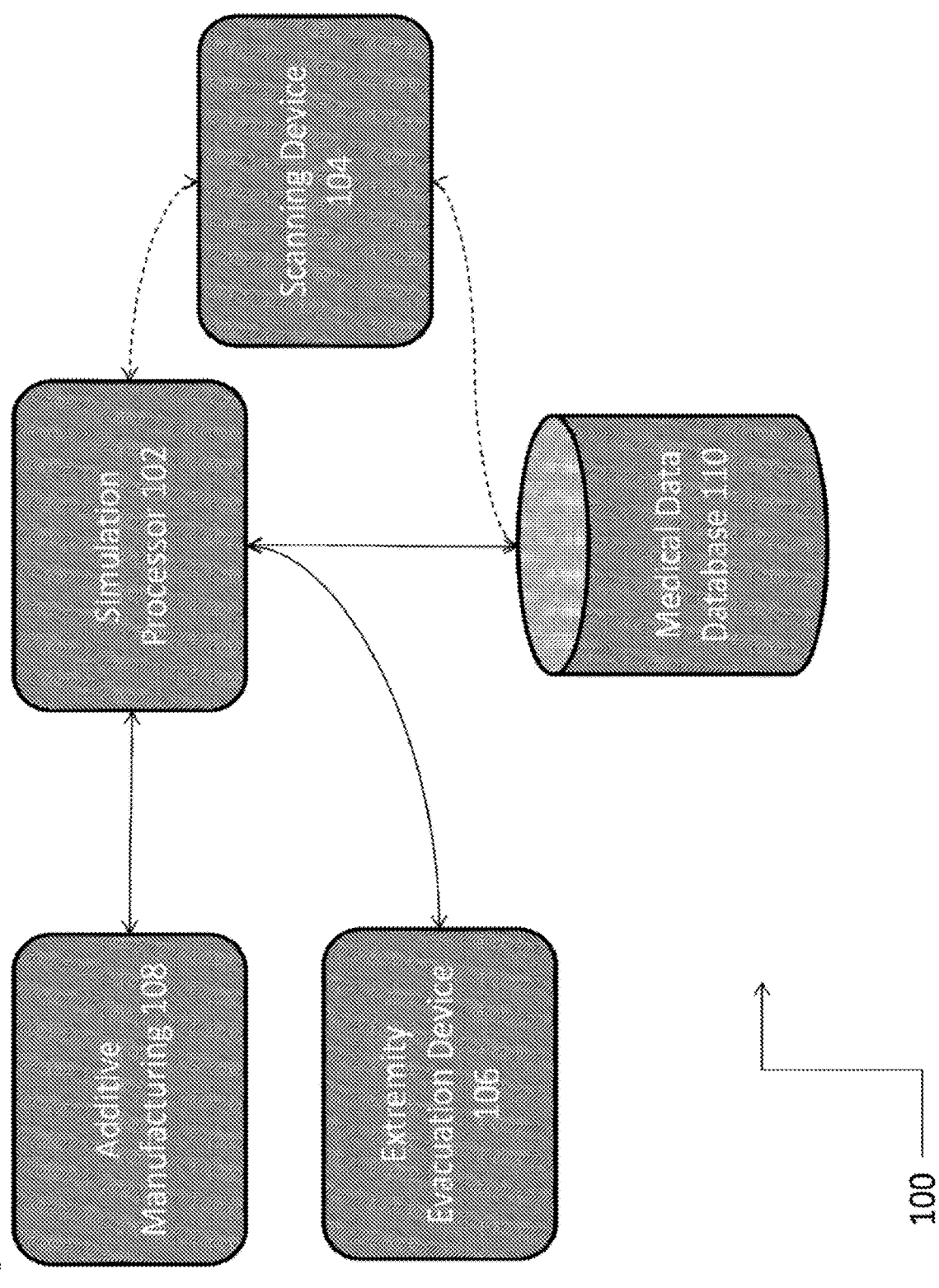
FIG. 1 is an overview block diagram detailing the arrangement of elements of the system described herein in accordance with one embodiment of the invention.

Turning to FIG. 1, a block diagram of the overall system 100 is provided. As shown, a simulation processor or computer 102 has connections (shown in solid or dotted lines) to a medical scanning device 104, a data repository (e.g. a medical record database) 110, an extremity excavation device 106 and an additive manufacturing device 108. In one embodiment, the connections between the different devices are wired or wireless connections implemented as a local area network (LAN). In an alternative embodiment, the connections between the various devices shown include Internet network connections and can include various routing and other network hardware, including but not limited to network gateways, exchanges, servers, routers, hubs and other network infrastructure necessary or useful for allowing various devices to connect to one another remotely and securely.

Simulation Processor

In a particular arrangement of elements provided, the simulation computer 102 is a processor configured to access and process data from the extremity sensing device 104, the medical data storage device 110, the extremity evacuation device 106 and/or the additive manufacturing device 108.

In a non-limiting example, the simulation computer 102 is a commercially available or custom built computer equipped with a one or more processors, graphical processing units, field programmable gate arrays, RAM and ROM memory, network interface adaptors and one or more input or output devices. In a further embodiment, the simulation computer 102 is a computer server or collection of computer servers, each server configured to store, access, process, distribute or transmit data between one another and other computers or devices accessible or connectable therewith. In still a further embodiment, simulation processor 102 is a hosted server, virtual machine, or other collection of software modules or programs that are interrelated and hosted in a remote accessible storage device (e.g. cloud storage and hosting implementation) that allows for dynamically allocated additional processors, hardware or other resources on an "as-need" or elastic need basis. In a further embodiment, the processor is configured to implement elastic load balancing algorithms to harness remote computing capacity or functionality to enable the system to handle computationally or otherwise resource intensive actions and procedures.

In a particular arrangement, the simulation processor 102 is a desktop or workstation computer using a commercially available operating system, e.g. Windows®, OSX®, UNIX or Linux based implementation. In a further configuration, the simulation processor 102 is a portable computing device such as an Apple IPad/IPhone® or Android® device or other commercially available mobile electronic device configured to have access to or implement remote hardware as necessary to carry out the functions described. In other embodiments, the simulation computer 102 includes custom or non-standard hardware configurations. For instance, the simulation computer 102 is a one or more micro-computer(s) operating alone or in concert within a collection of such devices, network(s), or array of other micro-computing elements, computer-on-chip(s), prototyping devices, "hobby" computing elements, home entertainment consoles and/or other hardware.

As provided herein, the simulation processor 102 is configured to access data obtained from a storage apparatus 110 corresponding to medical scans of an extremity of a patient using code executing in the processor(s).

Extremity Scan Data

In order to obtain data relating to the extremity of a patient, data regarding such an extremity is created by, or accessed from, a medical sensor device. For example, previous medical scans of an extremity, such as those obtained from a computerized axial tomography (CAT or CT) or magnetic resonance imaging (MM) scan are stored in a medical record storage apparatus 110. The medical record storage 110 is configured to store medical data, such as scan results, as well as other biometric data for a given patient (e.g. bone density, type, length, medical conditions etc.).

In one embodiment, the medical record storage 110 is a database, such as a NoSQL, SQL, or other flat, relational, object, or index types of database configured to store and provide access to data. Alternatively, the storage apparatus 110 is a file or data storage device, such as a remote hard drive, or storage apparatus. Regardless of the storage or database type, the medical record storage 110 also includes any necessary processors, components, control systems, network interfaces or other ancillary software or hardware necessary to transmit data between the medical record storage 110 and the simulation processor 102.

By way of non-limiting example, the scan data set contains a series of two-dimensional images obtained from the scanning device (e.g. CT scan slices). As such, the scan data set is a 3D dimensional representation of the scan data. As used throughout, the terms of pixel (denoting two dimensionality) and voxel (denoting three-dimensionality) with respect to irreducible display units of image or scan data set are used interchangeably and should not, when used, be considered to be limiting on the procedures or implementations described herein.

In arrangements where scan data, such as 3D data relating to CT, MM, planar radiographs, for an extremity is not stored in the medical record storage 110, the simulation processor 102 is configured to communicate, receive data directly, or pass instructions to a scanning device 104 having a processor (not shown) and bi-directional communication ability with either the simulation computer 102, the medical record storage device 110 or other gateway or interface.

In one embodiment, the scanning device 104 is a CT scanner, such as a high-resolution peripheral quantitative computed tomography (HR-pQCT) scanner or other medical device scanning apparatus. Without limiting the scope of the disclosure provided, HR-pQCT imaging permits the assessment of bone microstructure within the body. Data obtained by the high resolution scan are processed in a variety of ways to identify and characterize bone quality and strength. HR-pQCT scans provide imaging and other data representing cross-sectional analysis of microstructures on and within bone material that allows for increased precision and analysis of the extremity. In one or more embodiments, the data generated by a scan of the patient's extremity is converted by the processor of the scanning device into a 3D model of the bone structure within the scanned extremity that can be manipulated by a user. In another arrangement, the data obtained from the scanning device is transmitted directly or indirectly to the simulation computer 102 for processing.

The simulation computer 102 is further equipped with connections to transmit instructions to the extremity evacuation device 106. In one embodiment, the extremity evacuation device 106 is a surgical robot or other apparatus configured to receive instructions and data from local sensors, scanning devices, or uploaded instruction sets. Using this data, a processor(s) of the extremity extraction device are configured to implement a surgical procedure to autonomously, or semi-autonomously evacuate bone from an extremity.

In one non-limiting example, the extremity evacuation device 106 is a TSolution One® Surgical System, manufactured by Think Surgical of Fremont, California or another computer assisted tool for preparation of bone cavities and joint surfaces. In one or more arrangements, the extremity evacuation device 106 is used to remove bone or other material from a femur. For example, using an instruction set generated by the simulation computer 102 in the form of a CAD file, the extremity evacuation device 106 is configured to evacuate a cavity in the bone in areas having a pre-specified minimum thickness of cortical bone.

As an example, the extremity evacuation device 106 is a LBR iiwa Kuka robot manufactured by KUKA ROBOTICS Corporation of Shelby Township, Michigan. In a particular implementation, the extremity evacuation device 106 includes one or more selectable and/or selectively controllable evacuation devices. For instance, the extremity evacuation device 106 includes one or more bone saws, rasps, saws, drills, ablative devices and the like, each selectively addressable and controlled by one or more processors or electrical control units.

The simulation computer 102 is further equipped with connections to transmit instructions to the manufacturing device 108. In one or more embodiments, the additive manufacturing device 108 is a 3D printer device configured by a processor executing code therein to generate a physical model of a digital good or design. For example, the 3D printer 108 is configured to manufacture, a using the digital model of the implant generated by the simulation processor 102, a physical copy of the digital model. Typically, 3D printers generate physical models using filaments or other materials that can then be worked, painted or refined post manufacturing. However, medical grade 3D printers are also equipped to generate physical models using biocompatible materials, such as strong thermoplastics, metals and composite materials. In accordance with at least one aspect of the present invention, the additive manufacturing device is configured to generate physical models of the digital model using titanium. In alternative configurations, the physical model is formed of one or more of cobalt chromium, stainless steel, ceramic, and polymer composites. In a further implementation, the additive manufacturing device is configured to generate a single femoral implant, or a series of implant components that fit together as modular components. In one non-limiting example, modular components consist of different head dimensions and/or modular neck orientations. For example, the generated modular components are configured to attach to one another via a taper similar to a Morse taper.

By way of non-limiting example, the manufacturing device 108 is an electron beam melting based manufacturing device. Here, EBM techniques convert metal powders into a solid mass using an electron beam as the heat source. EBM based additive manufacturers manufacture parts by melting metal powder layer by layer with an electron beam in a high vacuum. This powder bed method produces dense metal parts directly from metal powder with characteristics of the target material. In one particular implementation, the EBM machine obtains a 3D CAD model and lays down successive layers of powdered material. These layers are melted together utilizing a computer controlled electron beam.

However, EBM devices encounter difficulty when manufacturing end products having small pore sizes. As an alternative, the manufacturing device 108 is a direct metal laser sintering additive manufacturing deices (DMLS). DMLS devices use high-powered lasers (such as Yb-fiber optic lasers) inside of a build chamber to fuse metal powder into solid parts by melting it using the focused laser beam. DMLS devices build up additively, using layers 20 micrometers thick. As a result, highly complex geometries can be automatically manufactured directly from the 3D data.

In a further embodiment, the 3D printer is capable of generating a titanium matrix or a material having a customized level of porosity sufficient to replicate the porosity of bone material. In one or more implementations, the manufacturing device is a milling device configured to mill a single work piece or work pieces into the appropriate dimensions. In a further arrangement, the manufacturing device is a mold press or other device configured to generate a stem having the appropriate dimensions.

Figure 2:
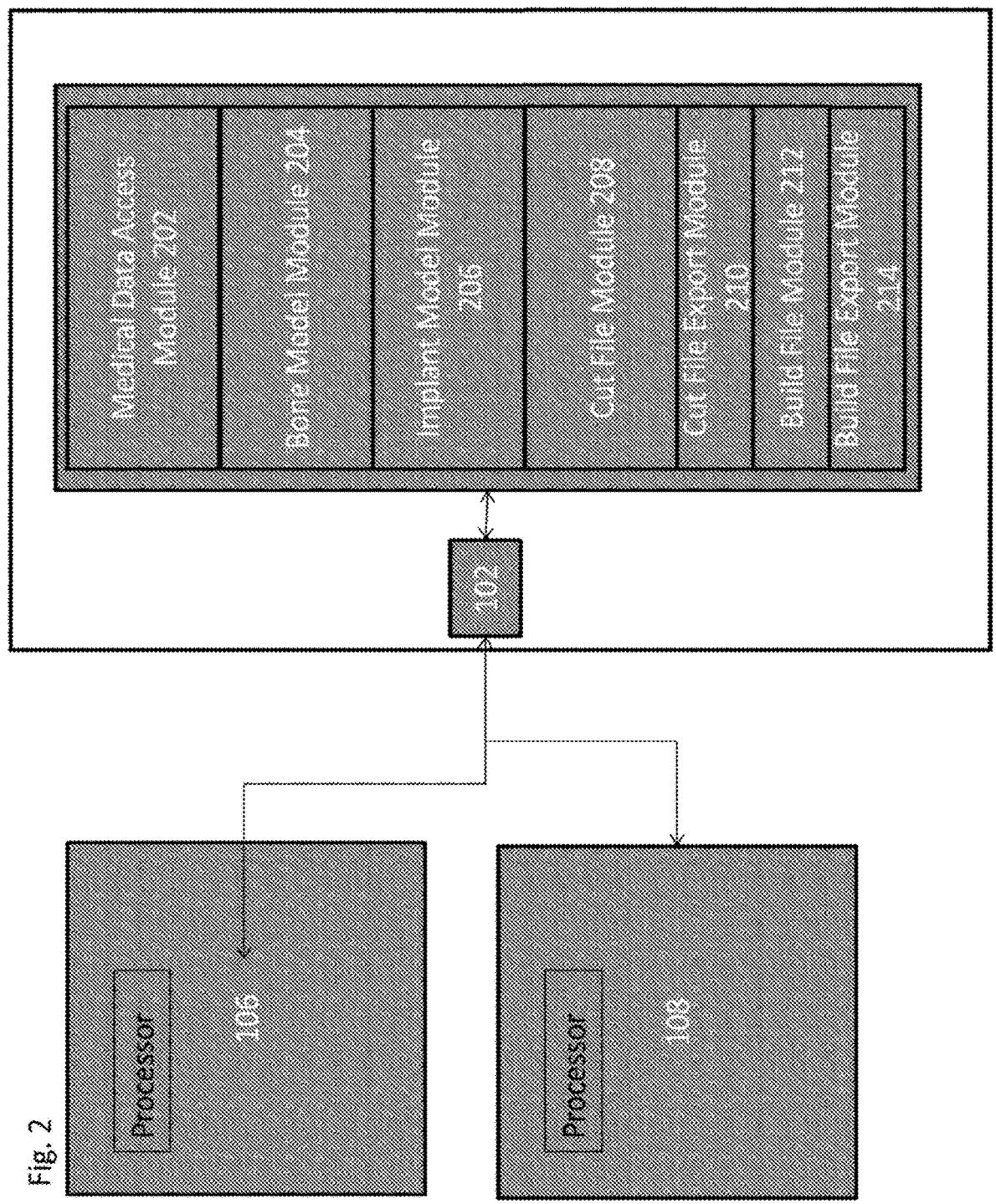
FIG. 2 is a block diagram detailing the interaction of specific elements of an embodiment as described herein.
Figure 3:
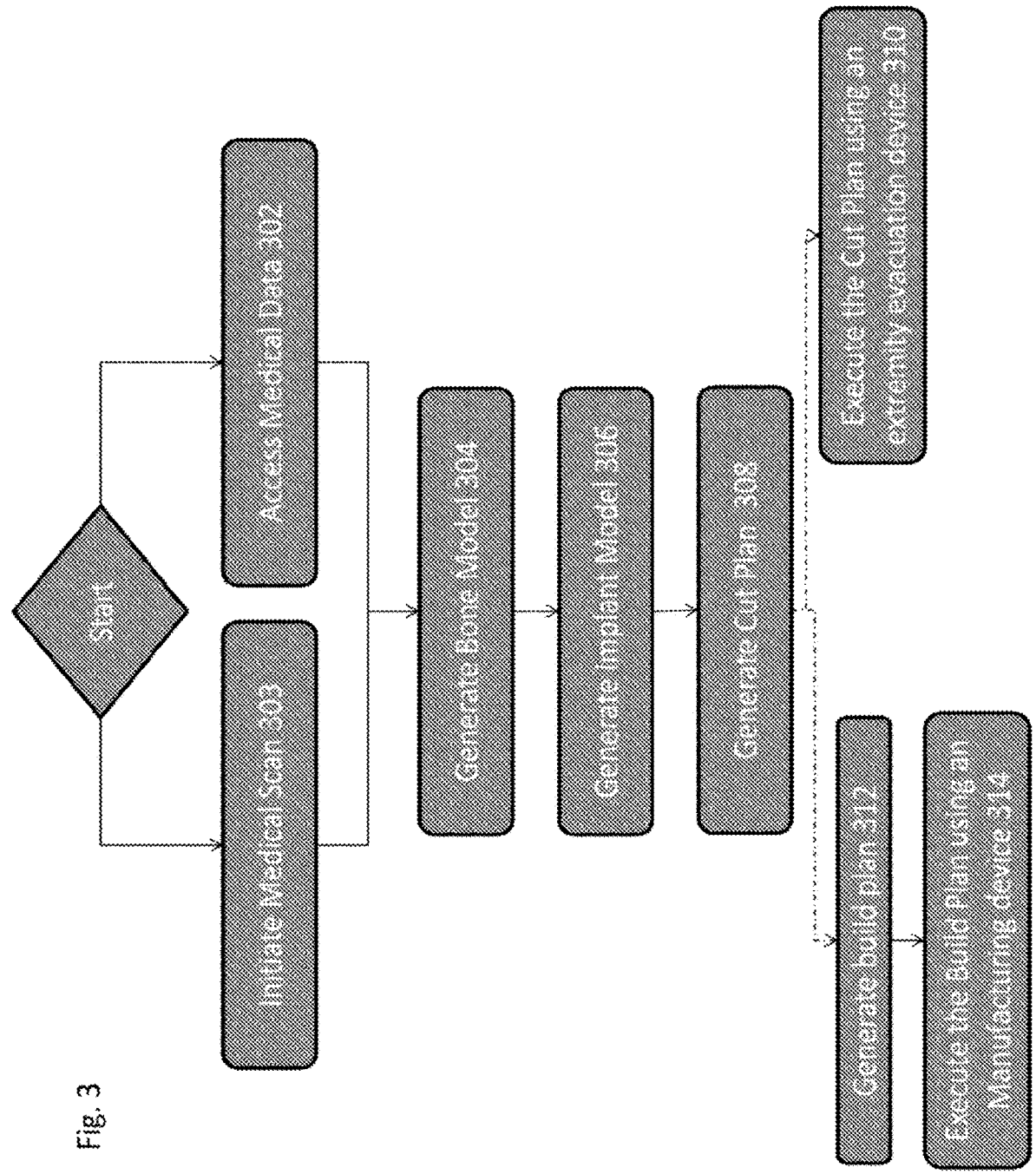
FIG. 3 is a flow diagram detailing the process of the example system in accordance with an embodiment of the present invention.

With reference to FIGS. 2 and 3, and for ease of description, the flow diagram of FIG. 2 and the block diagram of FIG. 3 provide an embodiment of the present system using the elements described. As shown in FIG. 2, a series of programmed steps performed by a properly configured computer system using one or more modules of computer-executable code can be used to implement the tasks of the processor 102.

As illustrated in FIG. 2, the system for generating a custom extremity implant includes accessing, using the simulation processor 102 configured by a medical data access model 202, data obtained from a medical record database 110, or from an active scan of a patient's extremity using an extremity scan device 104 as in steps 302-303.

For example, the simulation processor 102, using a medical data access module 202 configured as code executing therein, accesses scan data set obtained from an extremity scanning device 106 from a centralized medical records storage device or database 110. In one arrangement, the medical data access module 202 includes sub-modules for establishing and checking for a connection to a remote or local database. Potential additional submodules further include code executing within the processor for providing or requiring user credentials, encryption of data accessed, session management, or alerts or notification generation.

In an alternative configuration, as shown in step 303, the scan data set is obtained by the simulation processor 102 directly from a scanning device 104 or a storage device locally connected thereto. As an example, the medical data access module 202 configures the simulation processor 102 through one or more sub modules to access from an intermediate, temporary or permanent storage device data and/or files that are not accessible from the medical database 110. In this example, the submodules of the medical data access module 202 convey functionality to communicate with the scanning device directly, or through a common interface or gateway or by accessing, using specialty modules, the internal or accessible memory locations of the scanning device 104.

In a further implementation of the data access control module 202, the accessed data is encrypted or otherwise protected in order to maintain the privacy of the patient and/or to comply with regulations addressing medical data, such as HIPAA regulations. In the foregoing implementation, the data access module 202 further configures the simulation processor 102 to decrypt, decode or otherwise make available the protected data for further processing.

In both steps 302 and 303, the obtained data is at least in the form of imaging or other data corresponding to the extremity under analysis and is of sufficient quality to allow for the generation of a 3D digital model of the bone structure of the scanned extremity.

Turning to step 304, the simulation processor 102 is further configured to generate a virtual or digital representation of a bone or portion of a bone located within the scanned extremity. In one configuration, where the scan data set contains information detailing the surface and sub-surface features, density, and porosity of a bone of interest in the extremity (e.g. a femur), the bone model module 204 configures the simulation processor 102 to generate a model of the bone of interest that includes data values replicating or indicating the specific characteristics of the scanned bone.

Figure 8:
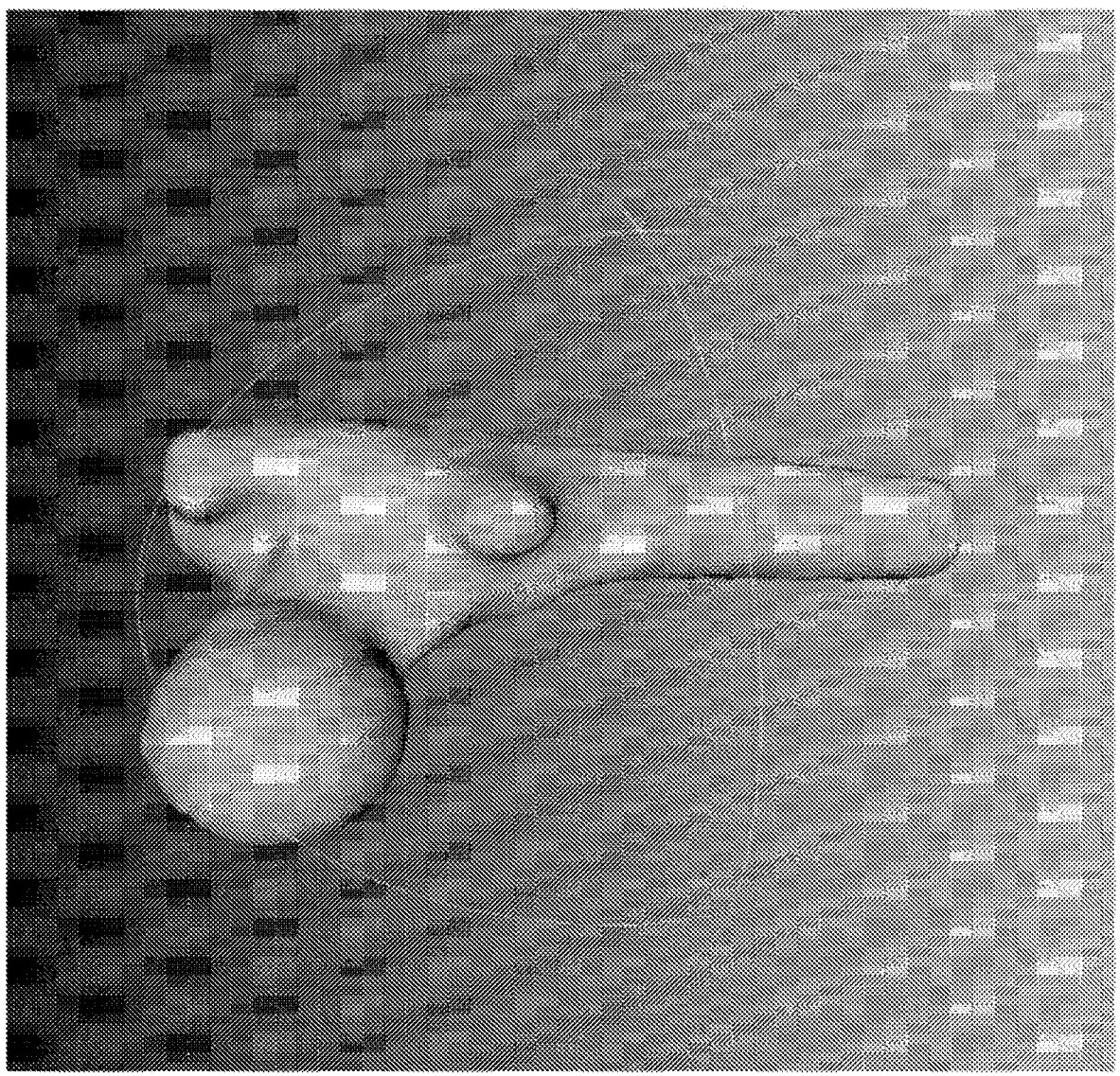
FIG. 8 provides a representative bone model generated according to broad aspects of the embodiments described herein.

In one particular implementation, a bone module 204 implemented as code executing in the simulation processor 102 causes the simulation processor 102 to utilize the scan data to create a single data object representing the scanned bone. For example, the simulation processor 102 is configured to generate a 3D model of the bone of interest as provided in FIG. 8. Alternatively, the bone model module 204 configures the simulation processor 102 to maintain the scan data set as a collection of linked, but discrete elements or files and utilize one or more orientation or transformation algorithms to present the scan data set as a single 3D object to a user.

In order to generate a 3D model useful for evaluating implants, the bone model module 204 includes one or more submodules or linked applications, code or instructions that configure the simulation processor 102 to identify and segment the voxels or pixels representing the femur from non-femur voxel data. In a further aspect, one approach to accomplishing this extracting a femur model from the scan data is to identify a space or void bounded by inner and outer regions. Here, the inner region represents the inner surface of the cortical bone, (e.g. where the cortical bone transitions to spongy bone) and the outer surface represents the outer surface of the cortical bone (where the cortical bone meets the periosteum). The inner surface is used to evaluate the fit of the generated implant while the outer cortical bone surface is instrumental to determining the inner bone model surface.

There are known rudimentary techniques to algorithmically identify the inner surface from scan data. However, algorithmically or automatically segmenting, in particular, the outer surface from the scan data set is not accomplished using prior art methods and techniques. Standard CT scans fail to achieve a high enough resolution to capture distinct inner and outer cortical bone boundaries. Automatically generating the bone model allows for the simulation processor 102 to identify the cortical bone boundaries with sub-voxel accuracy as well as resolve the thickness of the cortical bone region. More importantly, the generated bone model provides an improvement in fidelity and accuracy relative to the source raw scan data. That is, the bone model generated by the simulation processor 102 configured with the bone model module 204 provides a virtual representation of the femur, or any other scanned bone, that is more accurate relative to the physical dimensions of the bone than the raw scan data obtained from a typical scanning device.

In broad aspects, the bone model module 204 configures the simulation processor 102 to generate a bone model that accurately represents the inner and outer cortical bone surfaces for an individual patient. More importantly, the bone model module 204 configures the simulation processor 102 to generate the outer bone surfaces automatically from the raw scan data.

As an initial matter, the simulation processor 102 is configured by one or more submodules of the bone model module 204 to isolate the voxels representing the bone of interest (e.g. femur) from the background scan data. Those possessing the requisite level of skill in the art will appreciate that a number of different image recognition and pattern recognition techniques can be employed to segment the portion of the scan data set representing the femur from all other image data captured in the scan data set (e.g. skin, cartilage, non-femoral bone). Here, the simulation processor 102 is configured by one or more submodules of the bone model module 204 to segment the femur data from the remaining voxel data using a modified hybrid intensity-based and shape modeling segmentation approach.

Intensity-based techniques are not typically applied to femoral segmentation because intensity-based methods (the whole gamut of active contour segmentation, graph-cut based, and other thresholding-driven methods) rely on either a generally homogenous distribution of pixels within regions or well-defined gradients and edges that separate the object (e.g., femur) from the background (e.g., hip, tissue). In the proximal region the hip joint, however, some degree of degenerative joint disease (DJD) can both reduce the spacing between the hip and femur (causing segmentation masks to "bleed" into the hip) and amplify the partial volume effect (in which cortical bone intensities are lowered since cortical bone thickness is less than the resolution of the CT scan and individual voxel intensities are a blend of tissue and bone). This is evident most clearly in Cheng, Yuanzhi, Shengjun Zhou, Yadong Wang, Changyong Guo, Jing Bai, and Shinichi Tamura. "Automatic Segmentation Technique for Acetabulum and Femoral Head in CT Images." Pattern Recognition 46.11 (2013):2969-984., herein incorporated by reference as if provided in its entirety, where it is disclosed that researchers were able to achieve only a 64.5% "good" (characterized by an acceptable segmentation by a fully-trained third-party adjudicator) success rate. Additionally, Krcah, Marcel, Gabor Szekely, and Remi Blanc. "Fully Automatic and Fast Segmentation of the Femur Bone from 3D-CT Images with No Shape Prior." 2011 IEEE International Symposium on Biomedical Imaging: From Nano to Macro (2011): n. pag. herein, incorporated by reference as if provided in its entirety, also describes achieving an 81% success rate (equivalently adjudicated and defined as functional separation of the femur from the hip).

The failure cases are characterized by moderate to severe degrees of degenerative joint disease, demonstrating the limited range of patients adequately characterized by these methods. Within a targeted image processing task for a given intervention, the degree of disease should not functionally limit the application of an automated method for understanding the underlying patient-specific pathology.

Alternatively, active shape modeling (ASM) techniques provide robust generation of segmentation masks that ultimately resemble the "shape" of the femur, without any voxel tethering's to the hip and without any large deviations in shape. However, representative samples sampling the full range of underlying disease must be available to describe the mean shape and variance (with potential for higher moments of the femoral shape distribution), which can be a heavy front-end cost and be subject to significant statistical training biases and downstream generalization error to unseen or poorly sampled degrees of freedom in the model, especially during the initial registration process of a mean shape(s) to a patient-specific test data.

While ASM helps the segmentation mask be robust to low-density or highly osteoarthritic regions (in the present case, particularly around the femoral head), it can also lead to a less appropriate segmentation of regions of the femur with high variation (for example, femoral anteversion).

As such, there exists a need to achieve a high fidelity segmentation process that eliminates or minimizes the drawbacks of any one approach. Thus, the present approach to generating a bone model utilizes techniques that incorporate intensity-based concepts as well as shape encoding concepts resulting in a significant improvement upon both.

Figure 4A:
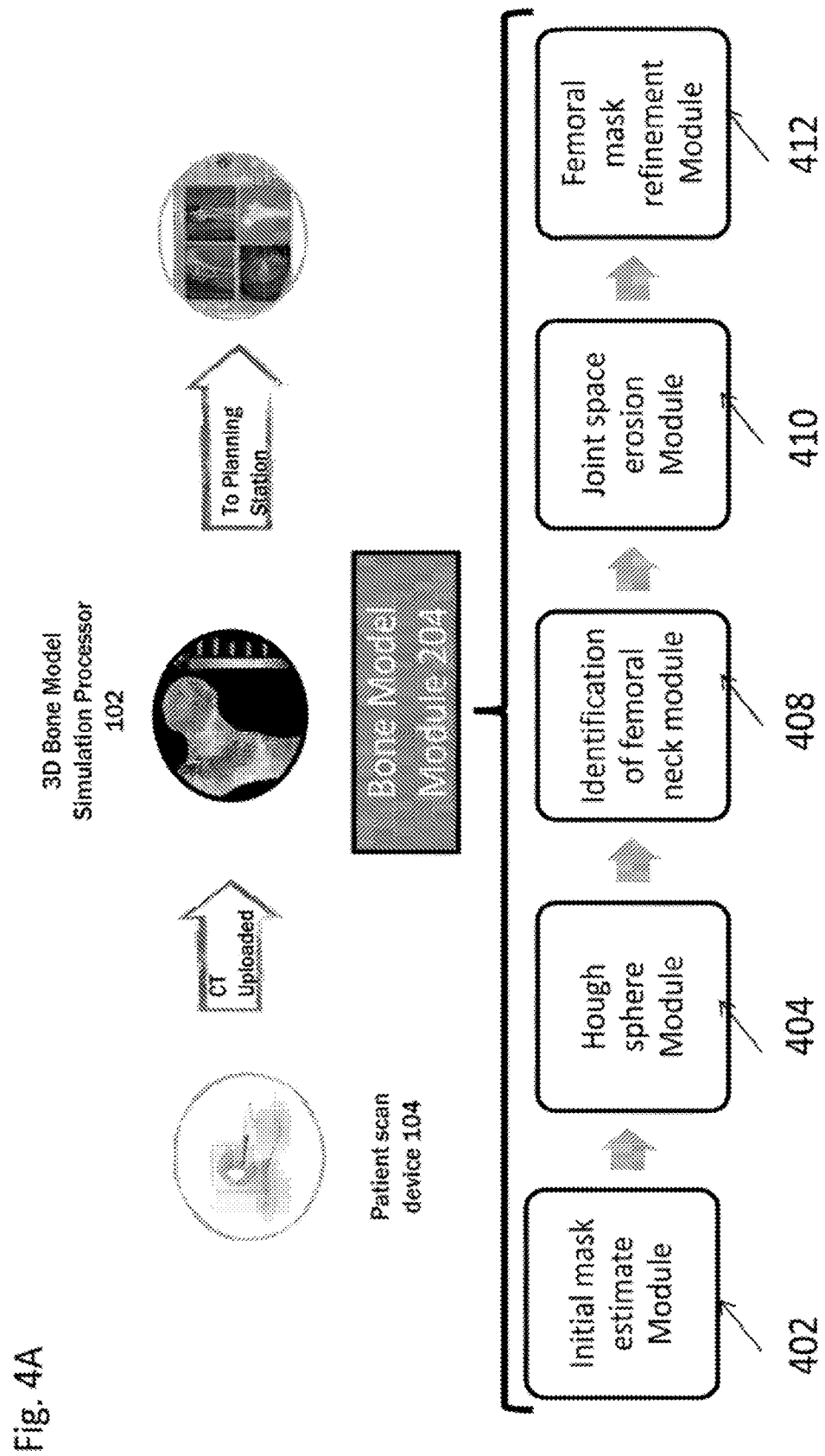

With reference to FIG. 4A, the bone model module 204 includes submodules that configure the simulation processor 102 to generate or isolate an initial mask estimate from the scan data set. For example, simulation processor 102 is configured to implement one or more morphological or other feature extraction algorithms to identify or segment the voxels depicting the femur in the scan data set from voxels not representing the femur. These segmentation algorithms can be functions or methods that obtain or identify contrast or intensity data in the scan data set in order to identify and segment the representation of the femur.

By way of non-limiting example, the simulation processor 102 is configured to generate an initial femur mask based on a thresholding technique using one or more initial mask estimate modules as shown in step 402. In a particular implementation, the simulation processor 102 evaluates the scan data set and generates an initial femoral mask using double thresholding. Here, high and low threshold values are used to determine the edge voxels of the initial mask by permitting those voxels over the high threshold to be classified as more strongly representing an edge of the femur than those voxels that are within the threshold range but do not exceed it. For instance, any voxel or pixel intensity value that exceeds the pre-determined threshold(s) is assigned or classified as femoral bone. The resulting mask of the voxels classified as bone is then used to generate a rough approximation of the femur in the scan data set. Alternative thresholding techniques commonly employed can also be used to generate an initial mask.

The mask generated according to step 402 is largely accurate in all regions except for those of low cortical intensity, which are primarily localized around the femoral head. Because of this imperfection, the present systems and methods employ additional steps to isolate the voxel data corresponding to the femur head. Because the femoral head, which is roughly spherical, is surrounded by a) femoral neck, b) the joint space, and potentially c) osteophytes that maintain some tethering to the acetabulum, the simulation processor 102 is further configured by one or more modules to identify the femoral neck and erode of all other voxel data to isolate and segment the femur.

Here, the simulation processor 102 is configured by a Houghsphere module 220 to implement a Hough transform so as to localize the femoral head as shown is step 404. To identify the spherical shape of the femoral head, a Hough transform, using a sphere as its initial shape, is applied to the scan data set so as to identify the femoral head. However, because the scan data spacing isn't necessarily equal in every plane, in an alternative implementation, an ellipsoid or "anisotropic" sphere, the semi-axes of which are set based on the scan spacing, is used by the simulation processor 102 as the shape of choice in the Hough transform instead of a sphere.

Figure 4B:
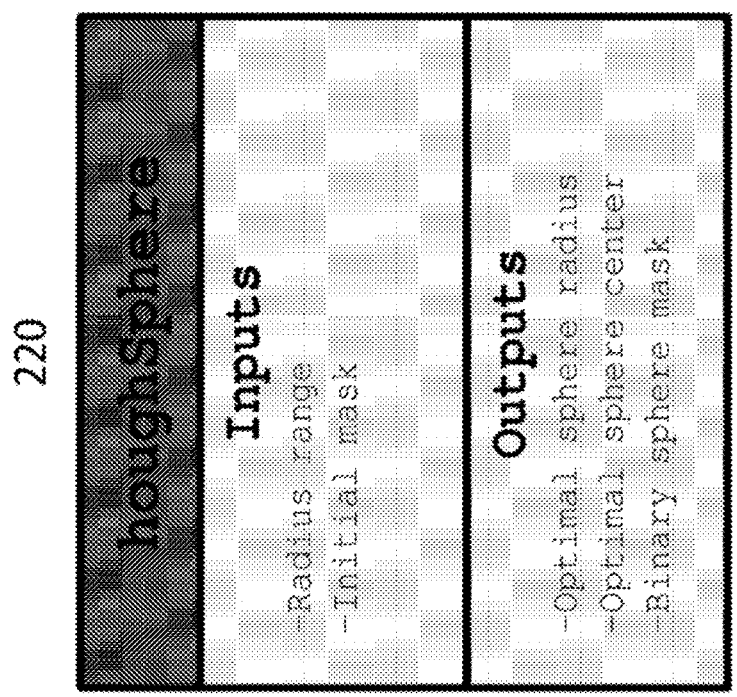

As shown in more detail in FIG. 4B, a Houghsphere module 220 configures the simulation processor 102 to accept input parameters such as the radius range of Hough circles, ellipsoids or spheres, as well as parameters defining the initial femoral mask. The simulation processor 102 executes the Hough transform algorithm in the form of code module 220, and generates values utilized to refine the initial femoral mask. By way of non-limiting example, the Houghsphere module 220 configures the simulation processor 102 to output sphere radius and center values. In a further implementation, these values represent optimized or otherwise refined data values. Additionally, in a particular implementation, the simulation processor 102 is configured by the Houghsphere module 220 to generate a binary sphere mask.

Because the acetabulum of the pelvis is also roughly hemispherical, and because the femoral head may be so thin that its initial mask may miss some regions, it is possible for the accumulator array in the Hough transform employed by the Houghsphere module 220 to actually fit the best Hough sphere to the acetabulum itself, rather than the femoral head. To avoid this particular issue, the simulation processor 102 is configured by one or more further modules to implement or apply one or more cost functions that operate to penalize the 4D hypersurface in the Hough space for larger radii. For instance, a cost function is implemented by the simulation processor 102 to penalize the 4D hypersurface in the Hough space for larger radii to an empirically determined power. In a further implementation, the simulation processor 102 is configured by the Houghsphere module 220 to identify the best fitting sphere for the femoral head instead of utilizing the native Hough sphere max function. By implementing the Houghsphere module 220, the simulation processor 102 is configured to generate from the scan data, an initial estimate for the location or position of the femoral head.

The initial segmentation of the femoral voxel data by using both the initial threshold mask and Hough Sphere fitting represents an improvement over a purely threshold or shape based segmentation and provides a bone model having investigatory value in and of itself. However, the segmentation procedures can be further refined further to identify and provide well-defined boundaries and edges so as to improve the accuracy of the resulting bone model.

The mask generated using the threshold mask module and refined by the Houghsphere module 220 is further refined by the simulation processor 102 configured by a femoral neck identification module, as shown in step 408. Here, Hough transforms are also used to identify femoral neck from the scan data set. More particularly, the femoral neck is identified, both in terms of proximity to the fitted Hough sphere (which represents the femoral head), as well as its bounds in 3D. This is achieved by segmentation of the Cartesian projection of a polar-coordinate derived image that visualizes the area around the femoral head with high resolution and fidelity, as demonstrated in FIGS. 6A and 6C.

In fact, because this image is derived from a polar representation, the joint space is, in a sense, redundantly amplified and makes it easier to segment the femoral neck. Given that the femoral neck is largely cylindrical, a suitably configured simulation processor 102 can achieve an adequate segmentation and isolation of the femoral neck in a manner that can be communicated to the segmentation mask of the femur for refinement. In this way, voxel linkages between the femoral mask and the hip caused by DJD (bone spurs, osteophytes, etc.), another major pitfall of intensity-based methods, can be prevented and an isolation of the femur between the hip can be maintained.

Figure 5A:
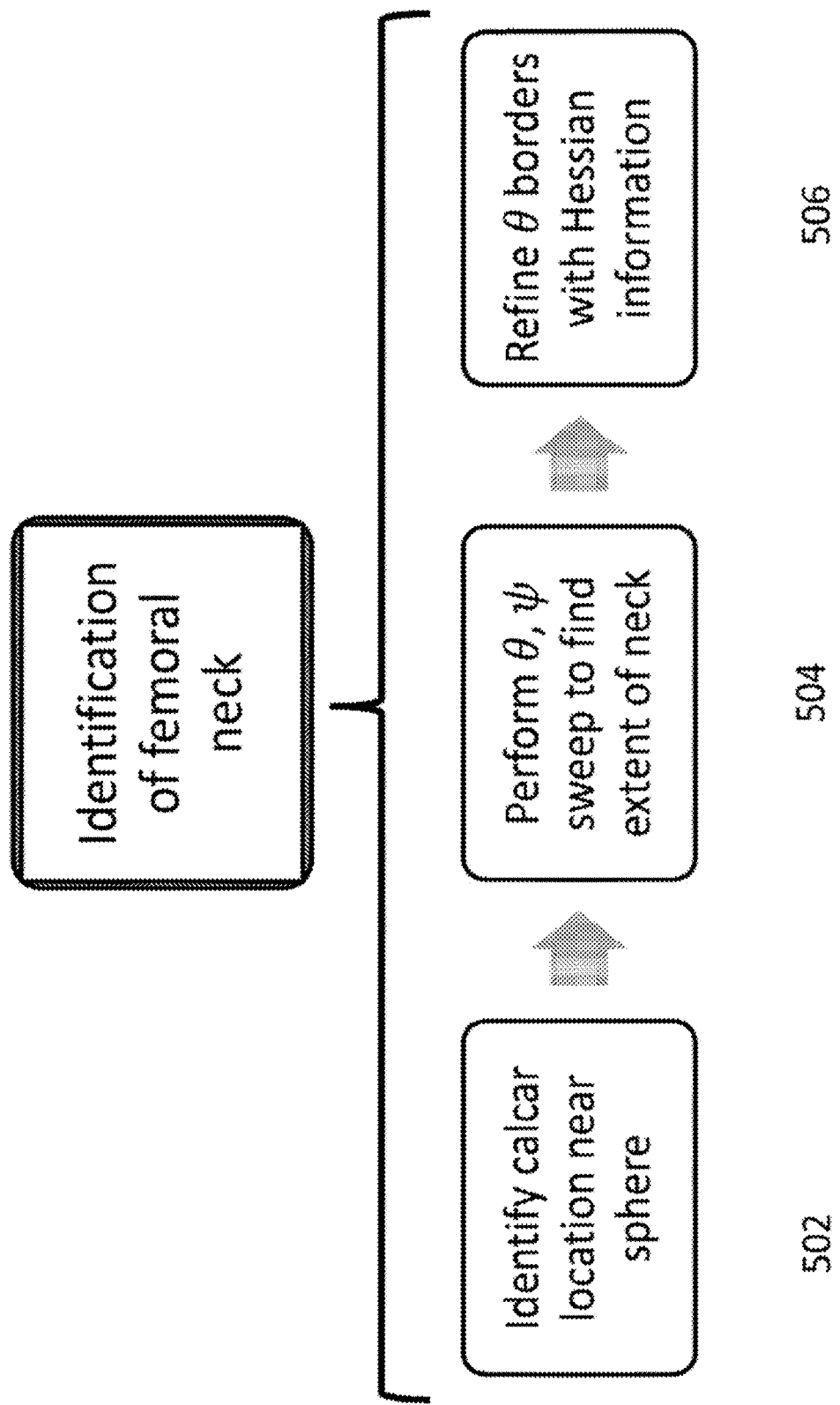
FIGS. 5A-B provide further particular details relating to the generation of a bone model of in accordance with aspects described herein.
Figure 5B:
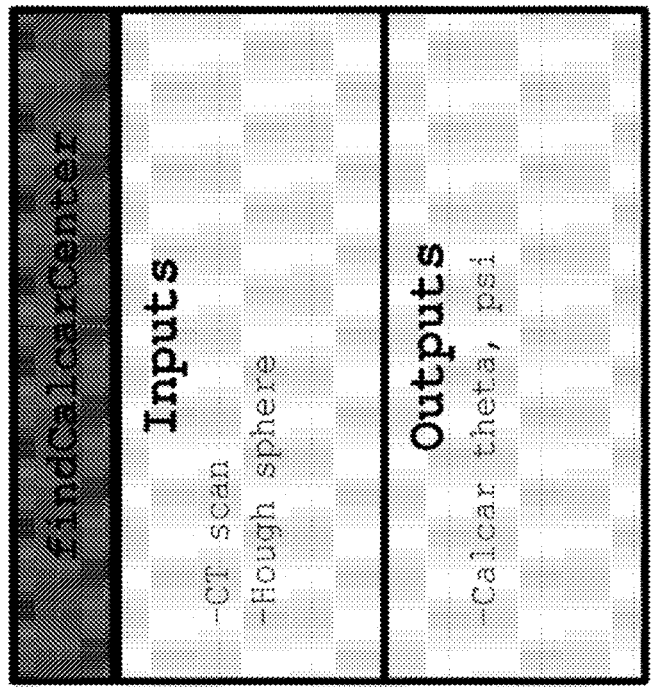

FIG. 5A provides an exemplar algorithm for identifying the femoral neck. Here, the simulation processor 102 is further configured by the femoral neck identification module to implement further steps to identify the femoral neck. For example, the simulation processor 102 is configured to identify the calcar location near the sphere (Hough Sphere) using a calcar identification module 222, as shown in step 502. Here, calcar refers to the vertically oriented bone present in the posteroemedial region of the femoral shaft inferior to the lesser trochanter of the femur. In one implementation, the calcar identification module 222 (shown in the module diagram of FIG. 5B) configures the simulation processor 102 to identify the calcar location by feature extraction, edge detection, or other pattern or image recognition algorithms configured to identify a pre-determined or pre-set morphological feature found within the scan data set. By identifying the calcar location, the simulation processor 102 is further configured to provide an estimate of the coordinate values of θ, ψ, which represent the center and bottom respectively of the femoral neck.

Once the a θ, ψ coordinate values have been identified, the values can be passed to a neck range module that configures the simulation processor 102 to manipulate the neck portion the femoral mask so as to ensure that it closely matches the actual scan data, as shown in step 504. For instance, the neck range module configures the simulation processor 102 to accept inputs such as, but not limited to, the θ, ψ coordinate values, as well as the raw scan data set and Hough sphere data. The simulation processor 102 generates a neck range (provided in new, updated or revised a θ, ψ coordinate values), along with a neck mask (or collection of voxels or voxels references), and a neck view.

Figure 6C:
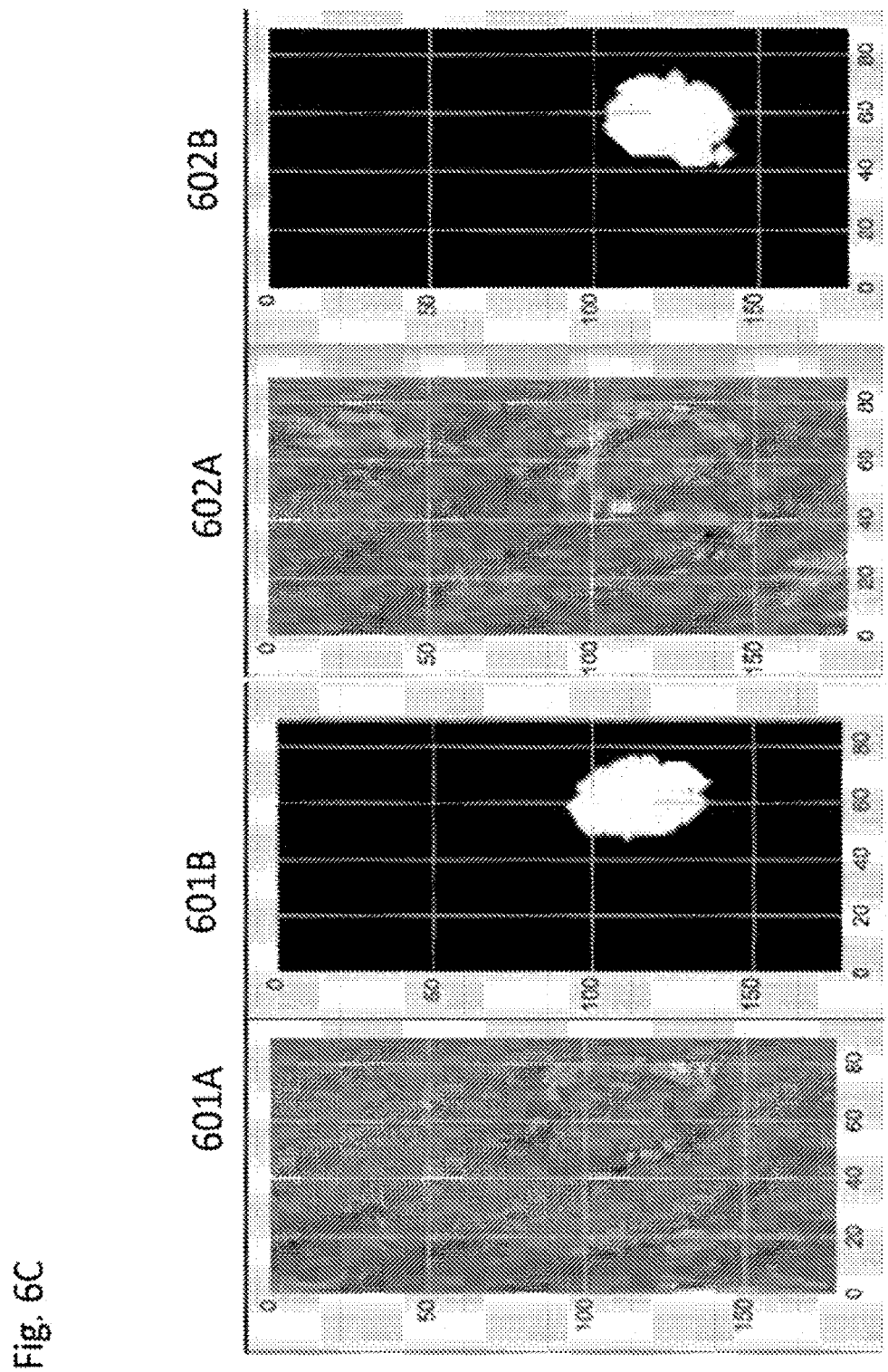

The results of the neck identification algorithm applied to the scan data can be found in FIGS. 6A and 6C. Here, a Cartesian projection of a polar-coordinate derived image of the region around the Hough sphere of two patients, one with low to moderate DJD (left image, 601A-B) and one with severe DJD (right image 602A-B), with the appropriate segmentation of the marrow cavity where the x-axis: psi (0-90°) and y-axis: theta (0-180°) is provided. The red high intensity region represents the calcar. The central region is the femoral neck, encapsulated with some padding by the acetabulum of the hip. As shown, the neck region is remarkably well differentiated relative to the traditional views of the CT scan (shown in greyscale).

As shown in FIG. 6B, the simulation processor 102 is optionally configured to implement a Hessian matrix calculation to identify the border regions around the region classified as the neck, as in step 506. In a further implementation, Hessian information is utilized when osteophytes are close to the acetabulum and generating irregularities in feature or blob identification algorithms. In a further implementation, the simulation processor 120 is further configured to implement a hybrid Laplacian and determinant of the Hessian operator (Hessian-Laplace) algorithm to determine the joint space. In this circumstance, inclusion of the Laplacian is useful, because joint space is expected to behave in such a manner (e.g. bone→space→bone).

Figure 11:
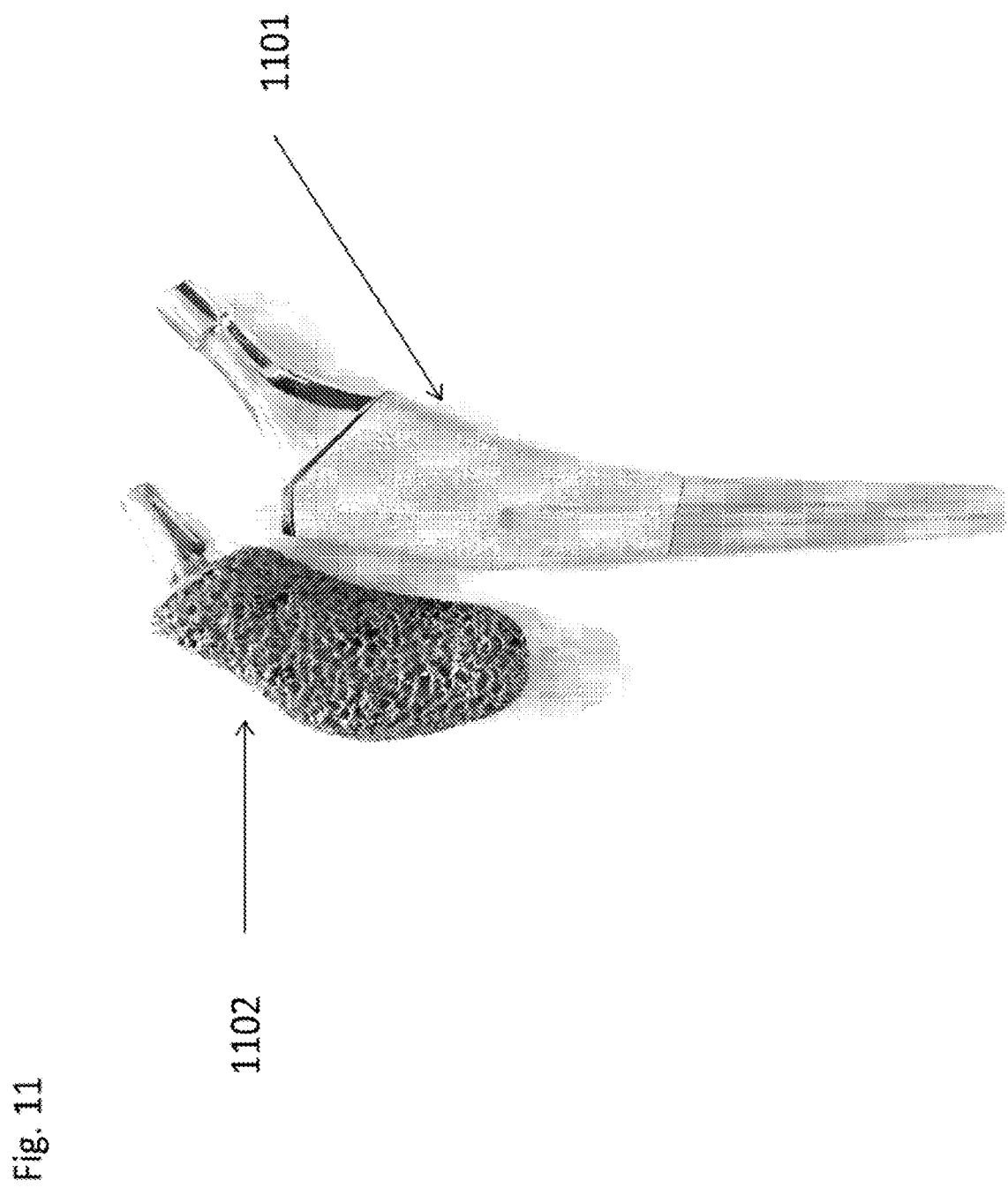
FIG. 11 provides a comparison of the implant generated according to broad aspects of the embodiments described herein and a prior art implant.

In addition to being useful in providing a complete and detailed bone model, the segmentation of the femoral head and neck also serves as source data for generating custom implants. As shown in FIG. 11, standard implants (1101) such as those depicted and provided by Stryker of Kalamazoo, Michigan, lack anteversion, or the natural tendency of the femoral head and neck to be positioned anterior relative to the body of the femur. By obtaining scan data on the femoral head and neck, the bone model can be used to generate custom implants 1102 that preserve the natural position of the patient's femoral head and neck so as to match a patient's biomechanical integrity. For example, by incorporating highly accurate femoral head and neck data into the bone model, an implant having the center of rotation in the biomechanically appropriate spot for a patient can be generated.

Figure 7:
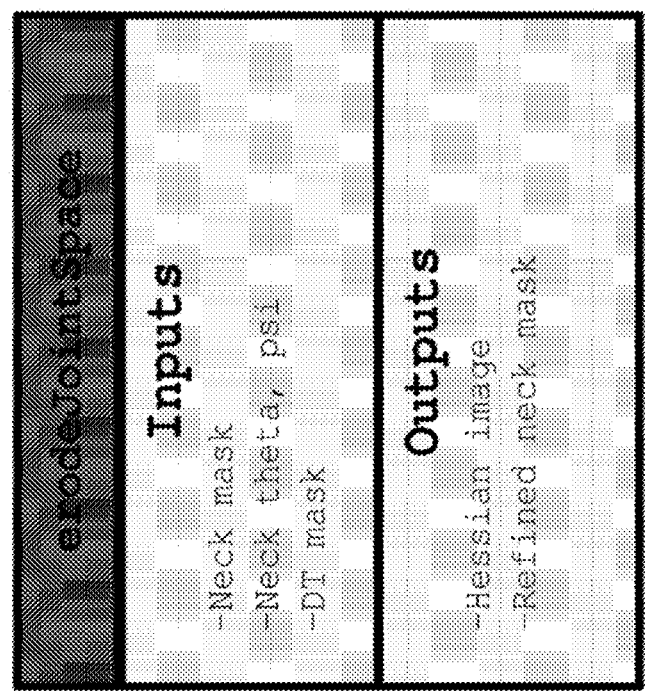
FIG. 7 provide a module diagram detailing a particular element described herein.

Returning to FIG. 4A, upon identification of the boundaries of the femoral neck, the joint space around the femoral head can be eroded to leave an isolated femoral mask as in step 410. As an example, the simulation processor 102 is configured by an Erosion Joint Space module 224 (FIG. 7). Here, the ErosionJoint Space module 224 configures the simulation processor 102 to receive neck mask data (such as pixel values or reference data) as well as θ, ψ coordinate values and DT mask values. The simulation processor 102 revises the scan data set so as to more clearly differentiate and highlight the border area about the neck region of the femur captured in the scan data set. Here, the Erosion Joint Space module 224 configures the simulation processor 102 to refine and identify the regions of the head and neck that are still bound to the acetabulum.

As shown in FIG. 4A, the generated mask, particularly the region around the Hough sphere, is "relaxed" using a femoral mask refinement module as in step 412. Here the simulation processor 102 is configured to refine the generated mask to fit around the actual femoral head. For example, morphological or convolutional operations, or other edge detection algorithms are employed to refine the generated mask to fit around the actual femoral head.

The processes of determining neck, head and joint space can be iteratively implemented to provide increasing refinements to the femoral mask. Additionally, any gradient based filtering, Fourier transform or other preprocessing step designed to improve the signal to noise ratio can be utilized in any of the foregoing steps.

As a result, a 3D bone model is generated through a hybrid intensity-based and shape fitting technique that avoids the pitfalls of both, while maintaining their advantages.

The bone model module 204 further comprises one or more submodules that configure the simulation processor 102 to undertake specific actions and implement specific functions to prepare the generated model for further use. For example, using one or more submodules, the bone model module 204 configures the processor 102 to generate or estimate data for missing features not found in the scan using statistical analysis or machine learning processes. Here, the simulation processor 102 is configured by the bone modeling module 204 to use finite element analysis to generate data on the porosity or density of an extremity. Alternatively, where portions of the scan data set are corrupted or unusable due to defect or specific circumstances, machine learning processes, such as support vector analysis, neural networking, or deep learning methodologies are implemented by the simulation processor 102 configured by the bone model module 204 to provide best fit or estimations of the missing data.

These output values (e.g. the complete bone model) are used, in part, to generate the dimensional values for any resulting implant generated according to the systems and steps described herein.

It will be appreciated that the aforementioned discussion is one application of the present invention, namely, for creation of a femoral stem implant. However, the bone modeling process described above can be used for other surgical sites and in particular, can be applied for other orthopedic implants, especially joint implants, such as for the shoulder, elbow, and knee.

Implant Model Generation

The 3D model of the bone structure generated by the bone model module 204 is used as the stage to evaluate the dimensions of a custom implant. Due to the detailed information presented by the virtual model of the patient bone structure, a medical professional is not limited in her selection of a preferred implant. Normally, medial implants, such as femoral stems used in hip angioplasty are selected from a common or standard size distribution of implants with little variation or customization available to individual patients and their unique anatomy or morphology. Using the digital representation of the bone structure (bone model), a medical professional is able to design a custom insert that maximizes the cortical bone contact between the bone and the inserted implant.

Ultimately, the surgeon will determine how long, (e.g. 10 cm the below the lesser trochanter) an implant stem will be based on the geometry of the cortical bone model. However, the implant generating process is bone conserving in and of itself. The bone model permits the minimization of cortical bone usage based on the patient, constraint and optimizations made during implant generation. For example, due to the precision of the bone model the generated implant can, in one non limiting example, have dimensions that range from 3-3.5 inches long, 4-4.5 inches wide and extending between 4 cm and 8 cm past the lesser trochanter. In contrast, as shown in FIG. 13, normal stems extend significantly past the lower trochanter.

When implants are placed in the bone, medical professions typically use manual planes and rasps or manual coring devices (as shown in FIG. 12) to generate an opening in the bone and contour the opening to accept the implant. As a result, the portion of the bone that is in contact with the implant can be as low as 30%. In turn, this requires a longer implant stem to ensure implant stability.

Figure 10:
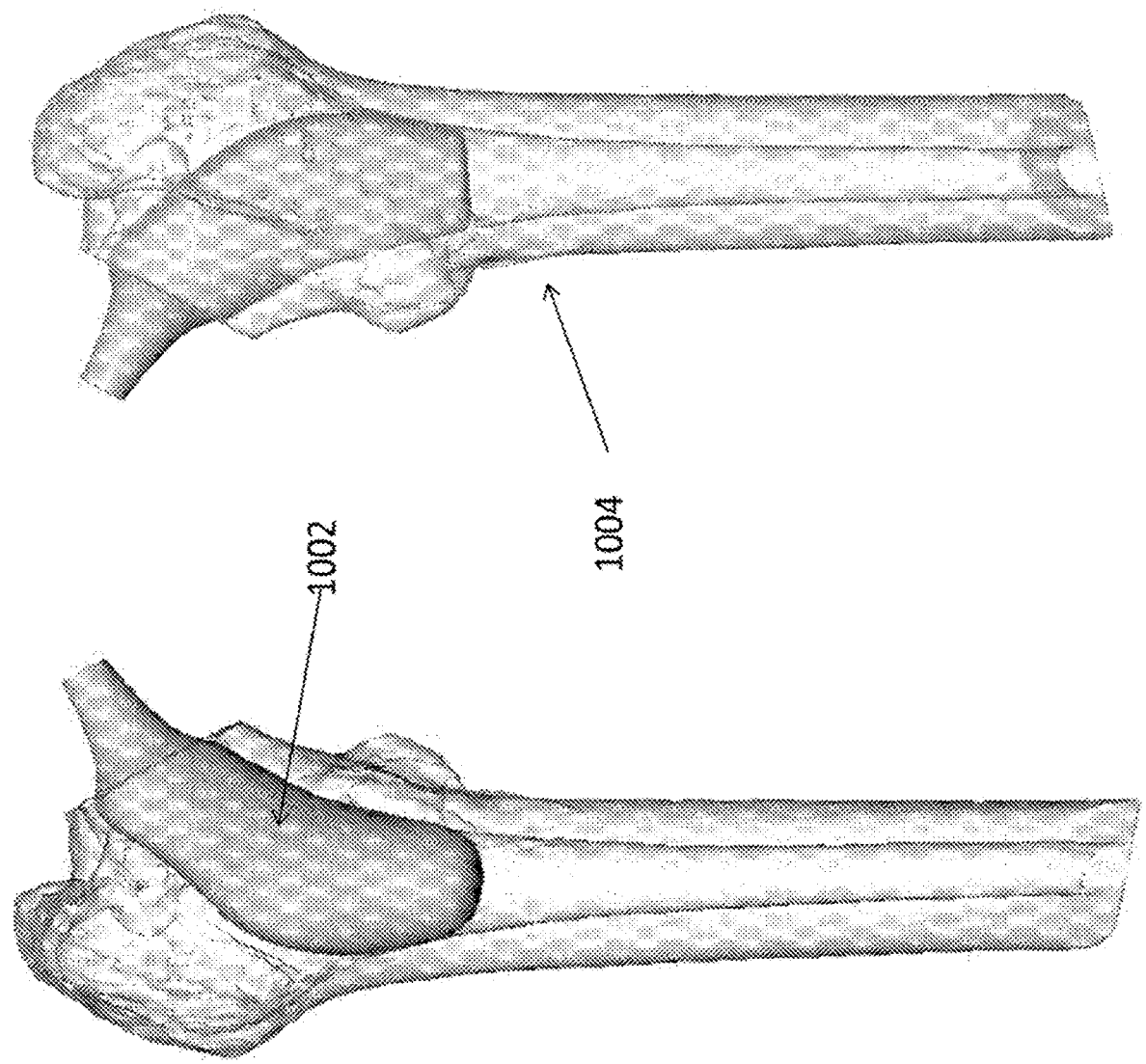
FIG. 10 provides a representative implant model interacting with a representative bone model generated according to broad aspects of the embodiments described herein.

In accordance with the system described, the virtual model of the bone is used to determine an improved implant that is designed to achieve a higher level of cortical contact. As shown in step 306, a digital representation of an implant is generated by the simulation processor 102, configured by an implant generation module 206, executing as code executing therein. The implant generation module 206 configures the simulation processor 102 to identify an optimal location for an implant. For example, though the use of an implant placement sub-module, the simulation processor 102 is configured to conduct an analysis of the virtual bone model and determine the optimal location for an implant based on minimal acceptable conditions. As an example, the simulation computer 102 identifies a location of the virtual model where an implant would encounter the most amount of cortical bone material upon insertion. Alternatively, the simulation processor is configured by one or more submodules to determine the location where the smallest or shortest implant could be inserted while maintaining the desired level of cortical bone contact, or other conditions. In a further example, shown in FIG. 10, the virtual stem model 1002 is placed in a location in the bone model 1004 where it is estimated that a minimum thickness of cortical bone will remain post excavation of the implant receptacle. In a further embodiment, the amount of bone remaining post-excavation is determined based on the cortical bone thickness values generated using scan data set obtained by the scanning device 104.

The implant generation module 206 further configures the processor 102 to make adjustments to the implant. In one arrangement, the implant model module 206 initially places a standardized implant within the bone module. However, once the initial placement has been determined, the implant module 206 configures the processor 102 to iterate over the dimensions and features of the implant model to obtain an implant having the desired characteristics. For instance, the implant generation module 206 configures the processor 102 to modify the implant model so as to generate an implant with a stem having a length that is less than or equal to the distance from the head of the femur to the lesser trochanter of the patient's femur as identified in the bone model. In an alternative configuration, the length of the stem extends no more than a pre-determined amount past the lower trochanter identified in the bone model.

In one or more arrangements, the generated model of the stem will have characteristics matching specific ranges or ratios of desired features to one another. In one or more arrangements the generated model of a femoral stem will have a length that is equal to the distance from the femur head to the base of lesser trochanter of the patient. In a further characteristic, the conformity of the implant will have at least 50%, or at least 60%, or at least 70%, or at least 80%, or at least 90%, or at least 95% available cortical bone contact. The custom implant, in one or more examples includes a stiffness characteristic determined by matching the pore size and % porosity of an additive manufacturing material to a patient's bone stiffness as measured by pre-op HR-pqCT scans and determined via finite element models implemented by the processor 102 configured by the bone model module 204. In a further arrangement, the stem will have a ratio of width to length of no more than about 1:3; however, this value is only exemplary in nature.

Figure 9:
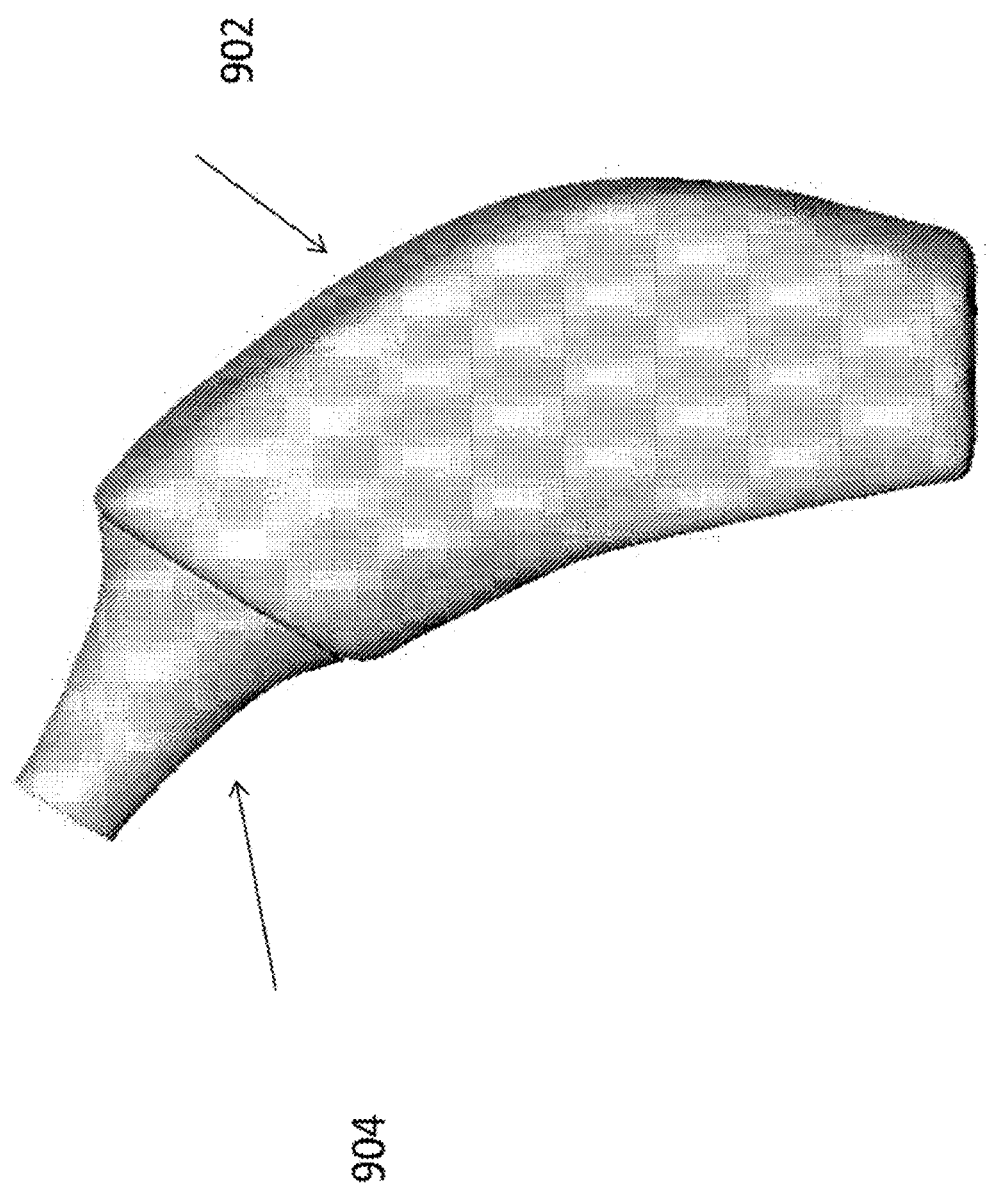
FIG. 9 provides a representative implant model generated according to broad aspects of the embodiments described herein.

As shown in FIG. 9, other characteristics of the implant, such as neck resection level, implant neck length, offset, anteversion and neck-shaft angle are optimized by the simulation processor 102 so, as in one embodiment, position the stem is such that the head of the implant 904 is at the center of rotation in a pre-planned spot to restore biomechanics. Likewise, other characteristics, such as insertability of the body of the implant 902 are also determined and customizable. Here, because of the highly conforming nature of the implant, those skilled in the art will appreciate that there can, in one or more configurations, be an area along the "shoulder" abutting the greater trochanter where 2 mm of overcut is planned. In one arrangement, a custom implant is designed such that the superior medial most aspect of the stem flares out 2 mm to circumferentially engage the neck upon final seating.

The simulation processor 102 is further configured by one or more implant module 206 sub-modules to adjustment the features of the implant to obtain an optimal placement. For example, one or more sub-modules of the implant model module 204 configure the processor to automatically, evaluate and reevaluate the placement of the implant in the bone model to determine if the placement meets optimal conditions. Thus, in one or more embodiments, the simulation processor engages in a maximization process to achieve the optimal desired characteristics of implant placement within the bone, and then a maximization process to optimize the characteristics of the implant itself in response. This process can, in certain embodiments, be conducted as an iterative process, such that it is repeated until a preferred placement and implant dimensions are achieved.

In an alternative embodiment, the iterative process is employed until desired implant configuration is placed in an area suitable for such an implant. For example, the implant model module 206, or a sub-module thereof, configures the processor 102 to iteratively adjust the size and placement of features of the digital model of the implant to achieve a compatibility with the bone model, where the compatibility is determined by the amount of available cortical bone exceeding a given threshold in a given location. For instance, the processor 102 is configured in one or more embodiments to optimize the characteristics of the implant such that implantation of the implant would leave at least a threshold amount of cortical bone intact. In a further non-limiting implantation, the implant model module 206 is configured to utilize a short stem implant in the iterative process.

In one additional arrangement, the implant model module 206 configures the processor 102 to automatically place the implant within the virtual model without user input. In an alternative configuration, the implant is placed by the processor 102 within the bone model, but such placement is configurable or modifiable by a user.

Once again, it will be appreciated that the aforementioned discussion is one application of the present invention, namely, for genertation of a femoral stem implant. However, the implant modeling process described above can be used for other surgical sites and in particular, can be applied for other orthopedic implants, especially joint implants, such as for the shoulder, elbow, and knee.

Bone Extraction Simulation

Upon finalization of the implant model as in step 306, the processor 102 is configured by a cut file module 208 to generate a series of actions to be executed by an extremity extraction device 106 to extract material from the extremity. In one particular non-limiting arrangement, the cut plan generation step 308 includes overlaying or integrating the finalized implant model with the bone model to determine the material to withdraw from the bone model so as to allow for an optimal fit between the bone and the implant. For example, the cut plan module 208 configures the processor 102 to evaluate the dimensions of the implant model and compare those dimensions against the dimensions of the bone model. Based on the comparison of the bone model and the implant model, those areas of the bone model that are within the boundaries of the implant are deleted and a void or cavity is introduced into the bone model.

By way of non-limiting example, assuming a 0.2 mm margin of error, the cut plan module 208 configures the processor 102 to generate cut files according to a number of pre-set parameters. For example, the generated cut plan will provide that any regions of cortical bone thicker than 3 mm will have 0.2 mm of bone removed. Additionally, regions having less than 3 mm cortical bone thickness will result in the bone being resected out to cortex. Furthermore, the cortex in the greater and lesser trochanteric regions will be bypassed and in the greater trochanteric area, the trabecular bone will be over resected by 1 mm.

The processor 102 is further configured, using the cut plan module 208, or sub-modules thereof to generate a data file that contains an instruction set for removing sufficient material from the extremity so as to permit the insertion of the implant as in step 307. In one arrangement, the data file is in a computer aided design (CAD) format. In another configuration, the data file is in a proprietary or custom data file format. In one or more implementations, the data file is generated and stored to a local or remote data storage device for retrieval or access by an extremity extraction device 106.

In a particular embodiment, the cut plan module 208 configures the processor to output a cut file in a format that is platform agnostic, such that the same file can be used by any number of properly configured the extremity evacuation devices 106 to evacuate the extremity.

In yet a further implementation, the cut file module 208 configures the processor 102 to access stored information relating to a specific make and model of extremity evacuation device, and generate a cut plan that incorporates specific tools, procedures or implementations that are present when the extremity evacuation device 106 is in operation.

The processor 102 is configured to store the cut file generated according to step 308 in a local or remote storage device for access by a processor or computer associated with the extremity extraction device 206. Alternatively, the cut file is sent directly to the extremity evacuation device 106 utilizing a cut file export module 210.

Use of the Bone Extraction File

In a further non-limiting arrangement, the processor 102 encrypts or otherwise protects the cut file prior to storage and provides a decryption key, use restriction or other mechanism that prevents the use of the cut file by unauthorized personnel or on a non-approved extraction device 106. In a further implementation, upon accessing the cut plan file, one or more checks or validations are run on the file to ensure that the integrity of the data has not been damaged and that the file is otherwise not corrupted prior to use.

In a further step, upon receipt of the cut file, the extremity evacuation device 106, configured by code executing in one or more processors associated therewith, utilizes the cut plan file to evacuate a suitably prepared extremity according to the details of the cut file. Thus, the extremity extraction device 106 executes a series of pre-programmed instructions that cause the extremity extraction device to, when properly oriented and prepared, to extract material or otherwise prepare the extremity for reception of an implant, as in step 310.

Additive Manufacturing of the Implant

Prior, subsequent or contemporaneously with the extraction of the material from the extremity, the processor 102 is further configured by a build file module 212 to generate, using data obtained from the implant build module 206, a series of instructions for building a physical copy of the implant model as provided by step 312. For example, the implant model module 206 provides a series of instructions for generating a physical copy of the simulated or virtual implant model as determined using data from the implant model module 206 generated in step 306. In one arrangement, the data file is a CAD file. However, in other arrangements, the data file is a custom or proprietary 3D printer file, or other file used with a standard, customized or modified additive printing apparatus. In an alternative configuration, the build plan is customized for a specific make, model or type of additive manufacturing device.

The processor 102 is configured to store the build file according to step 312 in a local or remote storage device for access by a processor or computer associated with the additive manufacturing device 108. Alternatively, the build file is sent directly to the additive manufacturing device 108 utilizing a build file export module 214.

Using the file generated in step 312, the additive manufacturing device 108, generates a physical replica of the digitally generated implant.

By way of further example, the implant generated is a patient specific femoral stem wherein the length of the stem does not exceed the length from the femur head to 2 mm below of the patient's lesser trochanter and is configured to achieve at least 60% available cortical bone contact. In a further arrangement, the patient specific femoral stem generated according the foregoing steps incorporate the dimensions, including the angle of the stem neck, so as to match the patient's femur head.

Once the extremity has been prepared and the implant replicated, a user is free to insert or otherwise equip a patient with the generated implant.

In one or more embodiments, the present invention also concerns a method for carrying out the foregoing actions described to generate a femoral implant. The method described includes the steps of scanning a femur of a patient using a 3D scanning device, wherein the scan is configured to provide information regarding the porosity and pore size of the scanned bone. The steps also include generating, using code executing in a processor, a 3D model of the femur, where the 3D model of the femur includes an extraction portion and a remaining portion; the extraction portion corresponding to a calculated amount of material to be removed from the femur. The method also includes building, using code executing in the processor, a 3D model of an implant configured to replace the extraction portion in the 3D model of the femur, wherein the 3D implant model is configured to match at least the porosity and pore size of the femur model using finite element analysis and outputting a cut file, wherein the cut file contains data on the material to be removed from the femur, and a make file, wherein the make file includes data on generating a physical copy of the 3D implant model for insertion into the remaining portion of the femur.

The method further includes, generating using a 3D printer executing a make file, a physical replica of the 3D model of the implant; and extracting using an autonomous bone extraction device configured with a cut file, material from the femur to allow for the insertion of the implant.

While this specification contains many specific embodiment details, these should not be construed as limitations on the scope of any embodiment or of what can be claimed, but rather as descriptions of features that can be specific to particular embodiments of particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated together in a single software product or packaged into multiple software products executed on one or more processors.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Publications and references to known registered marks representing various systems are cited throughout this application, the disclosures of which are incorporated herein by reference. Citation of the above publications or documents is not intended as an admission that any of the foregoing is pertinent prior art, nor does it constitute any admission as to the contents or date of these publications or documents. All references cited herein, including within the Figures, are incorporated by reference to the same extent as if each individual publication and references were specifically and individually indicated to be incorporated by reference.

While the invention has been particularly shown and described with reference to a preferred embodiment thereof, it will be understood by those skilled in the art that various changes in form and details may be made therein without departing from the spirit and scope of the invention.

What is claimed is:

1. A method for use in digitally generating a custom implant, the method comprising:
   generating a three-dimensional digital model of the custom implant using at least data operably identifying inner cortical bone surfaces obtained from a three-dimensional digital representation of a patient's bone having at least data operably identifying cortical bone boundaries of the patient's bone.

2. The method of claim 1, further comprising:
   generating the three-dimensional digital representation of the patient's bone, wherein the three-dimensional digital representation of the patient's bone comprises at least data operably identifying the cortical bone boundaries of the patient's bone.

3. The method of claim 2, wherein the generating the three-dimensional digital representation comprises obtaining a scan of the patient's bone.

4. The method of claim 2, wherein the generating the three-dimensional digital representation comprises:
   identifying and segmenting voxels or pixels representing the patient's bone from non-bone voxel or pixel data to allow for identification of the cortical bone boundaries.

5. The method of claim 4, wherein the identifying and segmenting comprises:
   segmenting bone voxel or pixel data from the remaining voxel or pixel data using a modified hybrid intensity-based segmentation method and an active shape modeling (ASM) segmentation method.

6. The method of claim 5, further comprising:
   isolating voxel or pixel data that corresponds to a portion of the patient's bone.

7. The method of claim 6, wherein the isolating voxel or pixel data comprises:
   implementing a Hough transform algorithm to localize a portion of the patient's bone.

8. The method of claim 7, further comprising:
   using a Hough transform algorithm to identify at least a portion of the patient's bone.

9. The method of claim 8, further comprising:
   eroding, upon identification of boundaries of the portion of the patient's bone, a joint space around the portion of the patient's bone to leave an isolated bone mask.

10. The method of claim 4, further comprising:
    generating an initial bone mask based on a double threshold technique that includes a high threshold value and a low threshold value that are used to determine edge voxels or pixels on the initial bone mask by classifying voxels or pixels that have values above the high threshold value as representing an edge of the patient's bone.

11. The method of claim 1, wherein the three-dimensional digital model of the custom implant comprises a percent contact between an inner surface of a cortical bone region of the patient's bone and an outer surface of the custom implant of at least 30%.

12. The method of claim 11, wherein the percent contact is at least 50%.

13. The method of claim 12, wherein the percent contact is at least 70%.

14. The method of claim 1, further comprising:
    identifying an optimal location for the custom implant by performing:
    (a) identifying a location of the three-dimensional digital representation of the patient's bone where the custom implant would encounter the greatest amount of cortical bone material upon insertion; or
    (b) identifying a location where the custom implant having a minimum length can be inserted while maintaining a predetermined level of cortical bone contact.

15. The method of claim 1, further comprising:
    identifying an optimal location for the custom implant by selecting a location of the three-dimensional digital representation of the patient's bone at which a minimum thickness of cortical bone will remain post excavation of a space for receiving the custom implant.

16. The method of claim 1, further comprising:
    manufacturing a physical copy of the three-dimensional digital model of the custom implant.

17. The method of claim 1, further comprising:
    generating a cut plan, based on both the three-dimensional digital representation of the patient's bone and on the three-dimensional digital model of the custom implant, which comprises a data file that contains an instruction set for removing bone from the patient so as to permit insertion of the custom implant.

18. A computer program product comprising a non-transitory computer readable storage medium readable by a processing circuit and storing instructions for execution by the processing circuit for performing the method of claim 1.

19. A system for generating a custom implant, the system comprising:
    a processor configured with code executing therein to transform digital bone data into a three-dimensional digital representation of a patient's bone, the processor further configured to generate, using an implant modeling application, a three-dimensional digital model of the custom implant for insertion into the bone, the three-dimensional digital representation of the bone including at least data operably identifying cortical bone boundaries of the patient's bone, the processor additionally configured to generate an excavation protocol for excavating bone from the selected bone such that a percent contact between an inner surface of a cortical bone region in the patient's bone and an outer surface of the custom implant is at least 30%; and a manufacturing device configured to generate the custom implant from the three-dimensional digital model of the custom implant.

20. The system of claim 19, further comprising:
a bone scanner that is configured to obtain bone data from the selected bone of the patient.

21. The system of claim 19, further comprising:
a processor controlled bone excavation device configured to excavate bone from the patient's bone according to an excavation protocol.

22. A computer implemented method for generating a three-dimensional digital model of a custom implant, the method comprising:
generating, using code executing in a processor, a three-dimensional digital model of a patient's bone using at least information obtained from a three-dimensional scan having at least data operably identifying cortical bone boundaries of the scanned bone of the patient, where the three-dimensional digital model of the patient's bone comprises an extraction portion and a remaining portion, the extraction portion corresponding to an anticipated removal of material from the bone; and
building, using code executing in the processor, a three-dimensional digital model of the custom implant configured to replace the extraction portion in the three-dimensional digital model of the patient's bone, wherein the three-dimensional digital model of the custom implant is configured to match the cortical bone boundaries features of the three-dimensional digital model of the patient's bone using finite element analysis.

23. The computer implemented method of claim 22, further comprising:
accessing a three-dimensional scan of the bone of the patient, wherein the scan is configured to provide information regarding the cortical bone boundaries of the scanned bone.

24. The computer implemented method of claim 22, further comprising:
outputting a cut file, wherein the cut file contains data on the material to be removed from the bone.

25. The computer implemented method of claim 24, further comprising:
extracting material from the bone using a computer control bone evacuation device configured to implement the cut file.

26. The computer implemented method of claim 24, further comprising:
outputting a make file, wherein the make file includes data on generating a physical copy of the three-dimensional digital model of the custom implant for insertion into the remaining portion of the bone.

27. A method for use in digitally generating a custom implant, the method comprising:
generating a three-dimensional digital model of the custom implant using at least data obtained from a three-dimensional digital representation of a patient's bone having at least data operably cortical bone boundaries of the patient's bone;
wherein the generating the three-dimensional digital representation comprises identifying and segmenting voxels or pixels representing the patient's bone from non-bone voxel or pixel data to allow for identification of the cortical bone boundaries; and
wherein the identifying and segmenting comprises segmenting bone voxel or pixel data from the remaining voxel or pixel data using a modified hybrid intensity-based segmentation method and an active shape modeling (ASM) segmentation method; or
further comprising generating an initial bone mask based on a double threshold technique that includes a high threshold value and a low threshold value that are used to determine edge voxels or pixels on the initial bone mask by classifying voxels or pixels that have values above the high threshold value as representing an edge of the patient's bone.

28. A method for use in digitally generating a custom implant, the method comprising:
generating a three-dimensional digital model of the custom implant using at least data obtained from a three-dimensional digital representation of a patient's bone having at least data operably cortical bone boundaries of the patient's bone; and
wherein the three-dimensional digital model of the custom implant comprises a percent contact between an inner surface of a cortical bone region of the patient's bone and an outer surface of the custom implant of at least 30%.

* * * * *